US010627326B2

(12) United States Patent
Rasmussen et al.

(10) Patent No.: US 10,627,326 B2
(45) Date of Patent: Apr. 21, 2020

(54) LIGAND-FUNCTIONALIZED SUBSTRATES WITH ENHANCED BINDING CAPACITY

(71) Applicant: 3M INNOVATIVE PROPERTIES COMPANY, St. Paul, MN (US)

(72) Inventors: Jerald K. Rasmussen, Woodville, WI (US); Catherine A. Bothof, Stillwater, MN (US); George W. Griesgraber, Eagan, MN (US); Semra Colak Atan, St. Louis Park, MN (US); James I. Hembre, Plymouth, MN (US); Robert T. Fitzsimons, Jr., Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/433,223

(22) Filed: Jun. 6, 2019

(65) Prior Publication Data

US 2019/0285523 A1    Sep. 19, 2019

Related U.S. Application Data

(62) Division of application No. 15/936,767, filed on Mar. 27, 2018, now Pat. No. 10,352,835, which is a division of application No. 15/023,729, filed as application No. PCT/US2014/057388 on Sep. 25, 2014, now Pat. No. 9,958,364.

(60) Provisional application No. 61/886,177, filed on Oct. 3, 2013.

(51) Int. Cl.

| | | |
|---|---|---|
| *B01D 71/44* | (2006.01) | |
| *G01N 1/40* | (2006.01) | |
| *C07K 1/34* | (2006.01) | |
| *C08J 7/18* | (2006.01) | |
| *C07F 9/38* | (2006.01) | |
| *G01N 33/544* | (2006.01) | |
| *C07K 1/18* | (2006.01) | |
| *B01D 67/00* | (2006.01) | |
| *B01D 71/52* | (2006.01) | |
| *B01D 71/56* | (2006.01) | |
| *B01J 20/26* | (2006.01) | |
| *B01J 20/28* | (2006.01) | |
| *B01J 20/32* | (2006.01) | |

(52) U.S. Cl.
CPC ......... *G01N 1/405* (2013.01); *B01D 67/0093* (2013.01); *B01D 71/44* (2013.01); *B01D 71/52* (2013.01); *B01D 71/56* (2013.01); *B01J 20/261* (2013.01); *B01J 20/28038* (2013.01); *B01J 20/321* (2013.01); *B01J 20/327* (2013.01); *B01J 20/3242* (2013.01); *B01J 20/3251* (2013.01); *B01J 20/3253* (2013.01); *C07F 9/3808* (2013.01); *C07K 1/18* (2013.01); *C07K 1/34* (2013.01); *C08J 7/18* (2013.01); *G01N 1/4077* (2013.01); *G01N 33/544* (2013.01); *B01D 2323/345* (2013.01); *B01D 2323/38* (2013.01); *B01D 2325/14* (2013.01); *B01D 2325/16* (2013.01); *C08J 2377/00* (2013.01); *G01N 2001/4088* (2013.01); *G01N 2333/924* (2013.01)

(58) Field of Classification Search
CPC ................... B01D 71/44; G01N 1/45
See application file for complete search history.

(56) References Cited

U.S. PATENT DOCUMENTS

| | | |
|---|---|---|
| 3,396,030 A | 8/1968 | Haas |
| 3,713,834 A | 1/1973 | Fitzgerald |
| 3,721,565 A | 3/1973 | Fitzgerald |
| 3,876,738 A | 4/1975 | Marinaccio |
| 3,928,517 A | 12/1975 | Knight |
| 4,157,418 A | 6/1979 | Heilmann |
| 4,539,256 A | 9/1985 | Shipman |
| 4,707,265 A | 11/1987 | Barnes, Jr. |
| 4,726,989 A | 2/1988 | Mrozinski |
| 4,867,881 A | 9/1989 | Kinzer |
| 5,120,594 A | 6/1992 | Mrozinski |
| 5,260,360 A | 11/1993 | Mrozinski |
| 5,344,560 A | 9/1994 | Sugo |
| 5,458,782 A | 10/1995 | Hou |
| 5,506,279 A | 4/1996 | Babu |
| 5,962,544 A | 10/1999 | Waller, Jr. |
| 6,056,529 A | 5/2000 | Meyering |

(Continued)

FOREIGN PATENT DOCUMENTS

| | | |
|---|---|---|
| EP | 0 142 810 | 5/1985 |
| JP | 47-040913 | 3/2009 |

(Continued)

OTHER PUBLICATIONS

Bamford, "Chemical Modification of Polymers Intended to Increase Blood Compatibility", Bull. Soc. Chim. Belg., 1990, vol. 99, No. 11-12, pp. 919-930.

(Continued)

*Primary Examiner* — Peter D. Mulcahy

(57) ABSTRACT

An article that can be used for biomaterial capture comprises
  (a) a porous substrate; and
  (b) borne on the porous substrate, a polymer comprising interpolymerized units of at least one monomer consisting of (1) at least one monovalent ethylenically unsaturated group, (2) at least one monovalent ligand functional group selected from acidic groups, basic groups other than guanidino, and salts thereof, and (3) a multivalent spacer group that is directly bonded to the monovalent groups so as to link at least one ethylenically unsaturated group and at least one ligand functional group by a chain of at least six catenated atoms.

4 Claims, No Drawings

(56) References Cited

U.S. PATENT DOCUMENTS

| | | | |
|---|---|---|---|
| 6,267,916 | B1 | 7/2001 | Meyering |
| 6,413,070 | B1 | 7/2002 | Meyering |
| 6,776,940 | B2 | 8/2004 | Meyering |
| 7,098,253 | B2 | 8/2006 | Rasmussen |
| 7,125,603 | B2 | 10/2006 | David |
| 7,338,692 | B2 | 3/2008 | Smith |
| 7,674,835 | B2 | 3/2010 | Rasmussen |
| 7,674,836 | B2 | 3/2010 | Rasmussen |
| 7,683,100 | B2 | 3/2010 | Rasmussen |
| 8,377,672 | B2 | 2/2013 | Rasmussen |
| 9,272,246 | B2 | 3/2016 | Rasmussen |
| 2010/0311850 | A1 | 12/2010 | Wickert |
| 2011/0033633 | A1 | 2/2011 | Bothof |
| 2011/0100916 | A1 | 5/2011 | Shannon |
| 2011/0217752 | A1 | 9/2011 | Rasmussen |
| 2012/0039920 | A1 | 2/2012 | Rasmussen |
| 2012/0252091 | A1 | 10/2012 | Rasmussen |
| 2015/0136698 | A1 | 5/2015 | Bothof |

FOREIGN PATENT DOCUMENTS

| | | |
|---|---|---|
| WO | WO 2003-046027 | 6/2003 |
| WO | WO 2007-078880 | 7/2007 |
| WO | WO 2009-148869 | 12/2009 |
| WO | WO 2010-096429 | 8/2010 |
| WO | WO 2013-162449 | 10/2013 |
| WO | WO 2013-184366 | 12/2013 |
| WO | WO 2014-052215 | 4/2014 |

OTHER PUBLICATIONS

Cook, "Effect of Cross-Link Density on Photoplasticity of Epoxide Networks Containing Allylic Dithioether Moieties", Macromolecules, 2012, vol. 45, No. 24, pp. 9734-9741.
Hubner, "Synthese und Reaktionen von 2-Alkenyloxazolonen", Die Angewandte Makromolekulare Chemie., 1970, vol. 11, No. 124, pp. 109-124.
Iwanade, "Protein Binding to Amphoteric Polymer Brushes Grafted onto a Porous Hollow-Fiber Membrane", Biotechnol. Prog. 2007, vol. 23, pp. 1425-1430.
Susanto, Photografted Thin Polymer Hydrogel layers on PES Ultrafiltration membranes: Characterization, Stability, and Influence on Separation Performance, Langmuir, 2007, vol. 23, pp. 7818-7830.
Taylor, "The Synthesis of Vinyl Peptide Monomers", Polymer Letters, 1969, vol. 7, pp. 597-603.
Ulbricht, "Advanced Functional Polymer Membranes", Polymer, 2006, No. 47, pp. 2217-2262.
Ulbricht, "Porous Polypropylene Membranes with Different Carboxyl Polymer Brush Layers for Reversible Protein Binding via Surface-Initiated Graft Copolymerization", Chem. Mater., 2005, vol. 17, No. 10, pp. 2622-2631.
Wang, "Influence of Pore Structure and Architecture of Photo-Grafted Functional Layers on Separation Performance of Cellulose-Based Macroporous Membrane Adsorbers", Journal of Chromatography A, 2009, vol. 1216, pp. 6490-6501.
Wente, "Manufacture of Superfine Organic Fibers", Naval Research Laboratories Report 4364, May 25, 1954, pp. 1-17.
Wente, "Superfine Thermoplastic Fibers", Industrial and Engineering Chemistry, Aug. 1956, vol. 48, No. 8, pp. 1342-1346.
International Search Report for PCT International Application No. PCT/US2014/057388 dated Jan. 19, 2015, 7 pages.
Supplementary European Search Report, EP Application No. 14851051, dated Apr. 24, 2017, 3 pages.

LIGAND-FUNCTIONALIZED SUBSTRATES WITH ENHANCED BINDING CAPACITY

CROSS REFERENCE TO RELATED APPLICATIONS

This application is a division of U.S. application Ser. No. 15/936,767, filed Mar. 27, 2018, now pending, which is a division of U.S. application Ser. No. 15/023,729, filed Mar. 22, 2016, which is a national stage filing under 35 U.S.C. 371 of PCT/US2014/057388, filed Sep. 25, 2014, which claims priority to U.S. Provisional Application No. 61/886,177, filed Oct. 3, 2013, disclosures of which are incorporated by reference in their entirety herein.

TECHNICAL FIELD

This invention relates to articles comprising ligand-functionalized substrates and, in other aspects, to processes for preparing and using the articles.

BACKGROUND

Detection, quantification, isolation, and purification of target biomaterials, such as viruses and biomacromolecules (including constituents or products of living cells, for example, proteins, carbohydrates, lipids, and nucleic acids) have long been objectives of investigators. Detection and quantification are important diagnostically, for example, as indicators of various physiological conditions such as diseases. Isolation and purification of biomacromolecules are important for therapeutic uses and in biomedical research.

Polymeric materials have been widely used for the separation and purification of various target biomaterials. Such separation and purification methods can be based on any of a number of binding factors or mechanisms including the presence of an ionic group, the size of the target biomaterial, a hydrophobic interaction, an affinity interaction, the formation of a covalent bond, and so forth.

Membrane-based technologies, especially in disposable format, are becoming increasingly important in biopharmaceutical and vaccine manufacturing processes. Membranes have been used in passive, size-based separations (for example, in virus removal applications) and, more recently, in active filtration (for example, for the removal of minor contaminants in later stages of purification processes).

Functionalized membranes (including functional polymer-bearing membranes) have typically suffered from relatively low biomaterial binding capacities, however, and this has generally limited their use in large-scale purifications. Porous beaded chromatography resins (bearing ion exchange or other interactive ligand functional groups), rather than functionalized membranes, therefore have been standardly used in "capture-and-elute" type protein purification processes.

SUMMARY

Thus, we recognize that there is a need for ligand-functionalized substrates (particularly, ligand-functionalized membranes) having relatively high biomaterial binding capacities. There is an accompanying need for ligand-functionalization processes that are relatively simple, cost-effective, and/or efficient (for example, involving relatively easily accessible starting materials and/or relatively few process steps).

Briefly, in one aspect, this invention provides an article that can be used for biomaterial capture. The article comprises (a) a porous substrate; and
(b) borne on the porous substrate, a polymer comprising interpolymerized units of at least one monomer consisting of (1) at least one monovalent ethylenically unsaturated group, (2) at least one monovalent ligand functional group selected from acidic groups, basic groups other than guanidino, and salts thereof, and (3) a multivalent spacer group that is directly bonded to the monovalent groups so as to link at least one ethylenically unsaturated group and at least one ligand functional group by a chain of at least six catenated atoms.

Preferably, the porous substrate is a porous membrane (more preferably, a porous polymeric membrane). The ligand functional group(s) are preferably selected from carboxy, phosphono, phosphato, sulfono, sulfato, boronato, tertiary amino, quaternary amino, and combinations thereof. The multivalent spacer group preferably comprises at least one hydrogen bonding moiety.

It has been discovered that relatively high binding capacity, ligand-functionalized substrates can be prepared by using certain monomers having a multiatom spacer group between the monomer's polymerizable group and ligand functional group. The monomers include ligand-functional, ethylenically unsaturated compounds in which at least one ligand functional group is separated or spaced from at least one ethylenically unsaturated group by a linking chain of at least six catenated atoms. When free radically polymerized, such monomers provide polymer bearing ligand functional groups that are separated or spaced from the resulting polymer chain or polymer backbone by the linking chain of at least six catenated atoms.

Surprisingly, the ligand functional groups of such polymers can be especially effective in interacting with target biomaterials. Porous substrates bearing the polymer (preferably, bearing grafted polymer) can exhibit unexpectedly higher biomaterial binding capacities than corresponding porous substrates bearing polymer derived from monomers in which the ligand functional group and the ethylenically unsaturated group are separated by a shorter linking chain. Binding capacities can be surprisingly further enhanced by including at least one hydrogen bonding moiety in the linking chain of the monomer.

Such ligand-functionalized substrates can be relatively easily prepared by utilizing free radical polymerization techniques and monomers derivable from readily available starting materials. The ligand-functionalized substrates can be used for various different applications, including the capture, binding, or purification of relatively neutral or charged biomaterials such as viruses and other microorganisms, proteins, cells, endotoxins, acidic carbohydrates, nucleic acids, and the like.

Thus, in at least some embodiments, articles of the invention comprising the above-described ligand-functionalized substrates can meet the above-cited need for ligand-functionalized substrates (particularly, ligand-functionalized membranes) having relatively high biomaterial binding capacities. In addition, article preparation processes of the invention, in at least some embodiments, can meet the accompanying need for ligand-functionalization processes that are relatively simple, cost-effective, and/or efficient (for example, involving relatively easily accessible starting materials and/or relatively few process steps).

In another aspect, this invention further provides a process for preparing the article of the invention. The process comprises
(a) providing a porous substrate; and
(b) providing the porous substrate with a polymer comprising interpolymerized units of at least one monomer consisting of (1) at least one monovalent ethylenically unsaturated group, (2) at least one monovalent ligand functional group selected from acidic groups, basic groups other than guanidino, and salts thereof, and (3) a multivalent spacer group that is directly bonded to the monovalent groups so as to link at least one ethylenically unsaturated group and at least one ligand functional group by a chain of at least six catenated atoms.

In yet another aspect, this invention also provides a process for capture or removal of a target biomaterial. The process comprises
(a) providing at least one article of the invention comprising at least one filter element; and
(b) allowing a moving biological solution containing a target biomaterial to impinge upon the upstream surface of the filter element for a time sufficient to effect binding of the target biomaterial.

In a further aspect, this invention additionally provides a free radically polymerizable compound or monomer consisting of (a) at least one monovalent ethylenically unsaturated group, (b) at least one monovalent ligand functional group selected from phosphorus-containing acidic groups, boron-containing acidic groups, and salts thereof, and (c) a multivalent spacer group that is directly bonded to the monovalent groups so as to link at least one ethylenically unsaturated group and at least one ligand functional group by a chain of at least six catenated atoms. Preferred compounds or monomers include those that can be represented by a Formula V, which can be obtained by replacing L in Formula I below with L', a heteroatom-containing group comprising at least one monovalent ligand functional group selected from phosphorus-containing acidic groups (preferably, phosphono or phosphato), boron-containing acidic groups (preferably, boronato), and salts thereof.

DETAILED DESCRIPTION

In the following detailed description, various sets of numerical ranges (for example, of the number of carbon atoms in a particular moiety, of the amount of a particular component, or the like) are described, and, within each set, any lower limit of a range can be paired with any upper limit of a range. Such numerical ranges also are meant to include all numbers subsumed within the range (for example, 1 to 5 includes 1, 1.5, 2, 2.75, 3, 3.80, 4, 5, and so forth).

As used herein, the term and/or means one or all of the listed elements or a combination of any two or more of the listed elements.

The words preferred and preferably refer to embodiments of the invention that may afford certain benefits under certain circumstances. Other embodiments may also be preferred, however, under the same or other circumstances. Furthermore, the recitation of one or more preferred embodiments does not imply that other embodiments are not useful, and is not intended to exclude other embodiments from the scope of the invention.

The term comprises and variations thereof do not have a limiting meaning where these terms appear in the description and claims.

As used herein, a, an, the, at least one, and one or more are used interchangeably.

The above Summary of the Invention section is not intended to describe every embodiment or every implementation of the invention. The detailed description that follows more particularly describes illustrative embodiments. Throughout the detailed description, guidance is provided through lists of examples, which examples can be used in various combinations. In each instance, a recited list serves only as a representative group and should not be interpreted as being an exclusive list.

Definitions

As used in this patent application:
"boronato" means a monovalent group of formula —B(OH)$_2$;
"carbonylimino" means a divalent group or moiety of formula —(CO)NR—, where R is hydrogen, alkyl (for example, selected from alkyl groups having from one to about four carbon atoms), or aryl (preferably, hydrogen);
"carboxy" means a monovalent group of formula —COOH;
"catenated atom" means an in-chain atom (rather than an atom of a chain substituent);
"catenated heteroatom" means an atom other than carbon (for example, oxygen, nitrogen, or sulfur) that replaces one or more carbon atoms in a carbon chain (for example, so as to form a carbon-heteroatom-carbon chain or a carbon-heteroatom-heteroatom-carbon chain);
"ethylenically unsaturated" means a group of formula —CY=CH$_2$ where Y is hydrogen, alkyl, cycloalkyl, or aryl;
"guanidino" means a monovalent group of formula R"$_2$N—C(=NR")NH— where each R" is independently hydrogen, hydrocarbyl, heterohydrocarbyl, or a combination thereof, and where any two or more R" groups optionally can be bonded together to form a ring structure (preferably, each R" is independently hydrogen, alkyl, cycloalkyl, heteroalkyl, aryl, heteroaryl, or a combination thereof; more preferably, each R" is independently hydrogen, alkyl, cycloalkyl, aryl, or a combination thereof);
"heteroatom" means an atom other than carbon or hydrogen;
"hydrogen bond acceptor" means a heteroatom selected from oxygen, nitrogen, and sulfur that has a lone electron pair;
"hydrogen bond donor" means a moiety consisting of a hydrogen atom covalently bonded to a heteroatom selected from oxygen, nitrogen, and sulfur;
"hydrogen bonding moiety" means a moiety comprising at least one hydrogen bond donor and at least one hydrogen bond acceptor;
"hydroxy" means a monovalent group of formula —OH;
"iminocarbonylimino" means a divalent group or moiety of formula —N(R)—C(O)—N(R)—, wherein each R is independently hydrogen, alkyl (for example, selected from alkyl groups having from one to about four carbon atoms), or aryl (preferably, at least one R is hydrogen; more preferably, both are hydrogen);
"iminothiocarbonylimino" means a divalent group or moiety of formula —N(R)—C(S)—N(R)—, wherein each R is independently hydrogen, alkyl (for example, selected from alkyl groups having from one to about four carbon atoms), or aryl (preferably, at least one R is hydrogen; more preferably, both are hydrogen);
"isocyanato" means a monovalent group of formula —N=C=O;
"oxycarbonylimino" means a divalent group or moiety of formula —O—C(O)—N(R)—, wherein R is hydrogen, alkyl (for example, selected from alkyl groups having from one to about four carbon atoms), or aryl (preferably, hydrogen);

"oxythiocarbonylimino" means a divalent group or moiety of formula —O—C(S)—N(R)—, wherein R is hydrogen, alkyl (for example, selected from alkyl groups having from one to about four carbon atoms), or aryl (preferably, hydrogen);

"phosphato" means a monovalent group of formula —OPO$_3$H$_2$;

"phosphono" means a monovalent group of formula —PO$_3$H$_2$;

"quaternary amino" means a monovalent group of formula —NR'$_3^+$, where each R' is independently hydrocarbyl, heterohydrocarbyl, or a combination thereof, and where any two or more R' groups optionally can be bonded together to form a ring structure (preferably, each R' is independently alkyl, cycloalkyl, heteroalkyl, heterocycloalkyl, aryl, heteroaryl, or a combination thereof; more preferably, each R' is independently alkyl, cycloalkyl, aryl, or a combination thereof);

"sulfato" means a monovalent group of formula —OSO$_3$H;

"sulfono" means a monovalent group of formula —SO$_3$H;

"tertiary amino" means a monovalent group of formula —NR'$_2$, where each R' is independently hydrocarbyl, heterohydrocarbyl, or a combination thereof, and where any two or more R' groups optionally can be bonded together to form a ring structure (preferably, each R' is independently alkyl, cycloalkyl, heteroalkyl, heterocycloalkyl, aryl, heteroaryl, or a combination thereof; more preferably, each R' is independently alkyl, cycloalkyl, aryl, or a combination thereof); and "thiocarbonylimino" means a divalent group or moiety of formula —(CS)NR—, where R is hydrogen, alkyl (for example, selected from alkyl groups having from one to about four carbon atoms), or aryl (preferably, hydrogen).

Monomers

Monomers suitable for use in preparing the article of the invention include those that consist of (a) at least one monovalent ethylenically unsaturated group, (b) at least one monovalent ligand functional group selected from acidic groups, basic groups other than guanidino, and salts thereof, and (c) a multivalent spacer group that is directly bonded to the monovalent groups so as to link at least one ethylenically unsaturated group and at least one ligand functional group by a chain of at least six catenated atoms. Preferably, the monomer(s) contain only moieties other than guanidino moieties. The monomers can be in a neutral state but can also be negatively (if acidic) or positively (if basic) charged under some pH conditions. The monomers can be permanently charged when the ligand functional group is in the form of a salt (for example, when the ligand functional group comprises quaternary ammonium or N-alkylpyridinium).

The monovalent ethylenically unsaturated group (as defined above) of the monomer(s) can be represented by the formula —CY=CH$_2$, wherein Y is hydrogen, alkyl, cycloalkyl, or aryl. Preferred ethylenically unsaturated groups include ethenyl, 1-alkylethenyl, and combinations thereof (that is, Y is preferably hydrogen or alkyl; more preferably, Y is hydrogen or C$_1$ to C$_4$ alkyl; most preferably, Y is hydrogen or methyl). The monomer(s) can comprise a single ethylenically unsaturated group or multiple ethylenically unsaturated groups (for example, two or three or up to as many as 6), which can be the same or different in nature (preferably, the same). The monomer(s) preferably have only one ethylenically unsaturated group.

The monovalent ligand functional group of the monomer(s) can be selected from acidic groups, basic groups other than guanidino, and salts thereof. Suitable ligand functional groups include those that exhibit at least a degree of acidity or basicity (which can range from relatively weak to relatively strong), as well as salts thereof. Such ligand functional groups include those commonly utilized as ion exchange or metal chelate type ligands.

Useful ligand functional groups include heterohydrocarbyl groups and other heteroatom-containing groups. For example, useful acidic or basic ligand functional groups can comprise one or more heteroatoms selected from oxygen, nitrogen, sulfur, phosphorus, boron, and the like, and combinations thereof. Useful salts of acidic groups include those having counter ions selected from alkali metal (for example, sodium or potassium), alkaline earth metal (for example, magnesium or calcium), ammonium, and tetraalkylammonium ions, and the like, and combinations thereof. Useful salts of basic groups include those having counter ions selected from halide (for example, chloride or bromide), carboxylate, nitrate, phosphate, sulfate, bisulfate, methyl sulfate, and hydroxide ions, and the like, and combinations thereof.

The monomer(s) can comprise a single ligand functional group or multiple ligand functional groups (for example, two or three or up to as many as 6), which can be the same or different in nature (preferably, the same). The ligand functional group(s) are preferably selected from carboxy, phosphono, phosphato, sulfono, sulfato, boronato, tertiary amino, quaternary amino, and combinations thereof. More preferred ligand functional group(s) include carboxy, phosphono, sulfono, tertiary amino, quaternary amino, and combinations thereof.

The multivalent spacer group of the monomer(s) can be directly bonded to the monovalent groups so as to link at least one ethylenically unsaturated group and at least one ligand functional group by a chain of at least six catenated atoms. Thus, the chain can comprise 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more catenated atoms (for example, including up to as many as 40 or 50). The chain preferably comprises at least seven catenated atoms (more preferably, at least eight; most preferably, at least nine, ten, eleven, or twelve) and/or comprises no more than about 30 catenated atoms (more preferably, no more than about 25; even more preferably, no more than about 20; most preferably, no more than about 16).

Although not wishing to be bound by theory, the length of the chain may contribute to adoption of helical or partially helical conformations by the polymer backbone (formed through monomer polymerization). When the chain is relatively short (for example, less than about six catenated atoms), ionic repulsion between charged ligand functional groups may force the polymer backbone into a random coil type conformation. As chain length increases, adoption of helical conformations may become possible and may be maximized at chain lengths of about 8-14 catenated atoms. A helical conformation of substrate-grafted polymer may facilitate presentation of the ligand functional group(s) for interaction with a target biomaterial.

Preferred multivalent spacer groups comprise at least one hydrogen bonding moiety, which is defined above as a moiety comprising at least one hydrogen bond donor and at least one hydrogen bond acceptor (both of which are heteroatom-containing, as described above). Thus, preferred multivalent spacer groups include heteroatom-containing hydrocarbon groups (more preferably, catenated heteroatom-containing hydrocarbon groups). More preferred spacer groups comprise at least two hydrogen bonding moieties or comprise at least one hydrogen bonding moiety and at least one hydrogen bond acceptor that is distinct from (not part of) the hydrogen bonding moiety.

Preferred hydrogen bonding moieties include those that comprise at least two hydrogen bond donors (for example, donors such as imino, thio, or hydroxy), at least two hydrogen bond acceptors (for example, acceptors in the form of carbonyl, carbonyloxy, or ether oxygen), or both. For example, an iminocarbonylimino moiety (having two N—H donors and at least two acceptors in the form of two lone electron pairs on carbonyl) can sometimes be preferred over a single iminocarbonyl moiety. Preferred spacer groups include those that comprise at least one iminocarbonylimino moiety (more preferably, in combination with at least one acceptor such as carbonyloxy), at least two iminocarbonyl moieties, or a combination thereof.

The hydrogen bond donor and hydrogen bond acceptor of the hydrogen bonding moiety can be adjacent (directly bonded) to each other or can be non-adjacent (preferably, adjacent or separated by a chain of no more than about 4 catenated atoms; more preferably, adjacent). The heteroatoms of the hydrogen bond donor and/or hydrogen bond acceptor can be located in the chain of catenated atoms of the spacer group or, alternatively, can be located in chain substituents.

Although hydrogen bond donors can also function as hydrogen bond acceptors (through a lone electron pair of the donor's heteroatom), the hydrogen bonding moiety preferably comprises distinct donor and acceptor moieties. This can facilitate intramolecular (intermonomer) hydrogen bond formation. Although not wishing to be bound by theory, such intramolecular hydrogen bonds between adjacent monomer repeat units in the polymer molecule may contribute to at least a degree of multivalent spacer group stiffening, which may facilitate presentation of the ligand functional group(s) for interaction with a target biomaterial.

Preferred hydrogen bonding moieties include carbonylimino, thiocarbonylimino, iminocarbonylimino, iminothiocarbonylimino, oxycarbonylimino, oxythiocarbonylimino, and the like, and combinations thereof. More preferred hydrogen bonding moieties include carbonylimino, iminocarbonylimino, oxycarbonylimino, and combinations thereof (most preferably, carbonylimino, iminocarbonylimino, and combinations thereof). Preferred multivalent spacer groups include those that are divalent, trivalent, or tetravalent (more preferably, divalent or trivalent; most preferably, divalent).

A class of useful monomers includes those represented by the following general formula $$CH_2=CR^1-C(=O)-X-R^2-[Z-R^2]_n-L \qquad (I)$$

wherein $R^1$ is selected from hydrogen, alkyl, cycloalkyl, aryl, and combinations thereof;

each $R^2$ is independently selected from hydrocarbylene, heterohydrocarbylene, and combinations thereof;

X is —O— or —NR$^3$—, where $R^3$ is selected from hydrogen, hydrocarbyl, heterohydrocarbyl, and combinations thereof;

Z is heterohydrocarbylene comprising at least one hydrogen bond donor, at least one hydrogen bond acceptor, or a combination thereof;

n is an integer of 0 or 1; and

L is a heteroatom-containing group comprising at least one monovalent ligand functional group selected from acidic groups, basic groups other than guanidino, and salts thereof.

Preferably, $R^1$ is hydrogen or alkyl (more preferably, hydrogen or $C_1$ to $C_4$ alkyl; most preferably, hydrogen or methyl); each $R^2$ is independently hydrocarbylene (more preferably, independently alkylene); X is —O— or where $R^3$ is hydrogen; Z is heterohydrocarbylene comprising at least one moiety selected from carbonyl, carbonylimino, carbonyloxy, ether oxygen, thiocarbonylimino, iminocarbonylimino, iminothiocarbonylimino, oxycarbonylimino, oxythiocarbonylimino, and combinations thereof (more preferably, selected from carbonyl, carbonylimino, carbonyloxy, ether oxygen, iminocarbonylimino, oxycarbonylimino, and combinations thereof; even more preferably, selected from carbonylimino, carbonyloxy, ether oxygen, iminocarbonylimino, and combinations thereof; most preferably, selected from carbonylimino, iminocarbonylimino, and combinations thereof); n is an integer of 1; and/or L is a heteroatom-containing group comprising at least one ligand functional group selected from carboxy, phosphono, phosphato, sulfono, sulfato, boronato, tertiary amino, quaternary amino, and combinations thereof (more preferably, selected from carboxy, phosphono, sulfono, tertiary amino, quaternary amino, and combinations thereof).

Such monomers can be prepared by known synthetic methods or by analogy to known synthetic methods. For example, amino group-containing carboxylic, sulfonic, or phosphonic acids can be reacted with ethylenically unsaturated compounds that comprise at least one group that is reactive with an amino group. Similarly, ligand functional group-containing compounds that also contain a hydroxy group can be reacted with ethylenically unsaturated compounds that comprise at least one group that is reactive with a hydroxy group, optionally in the presence of a catalyst. Preferred monomers are (meth)acryloyl-functional. (As used herein, the term "(meth)acryloyl-functional" refers to acryloyl-functional and/or methacryloyl-functional; similarly, the term "(meth)acrylate" refers to an acrylate and/or a methacrylate).

Representative examples of useful monomers include those derived from the reaction of an alkenyl azlactone of general Formula II

or an ethylenically unsaturated isocyanate of general Formula III $$CH_2=C(R^1)-C(=O)-X-R^2-N=C=O \qquad (III)$$

with a ligand functional group-containing compound of general Formula IV $$H-X-R^2-L \qquad (IV)$$

to produce monomer of general Formula I (wherein $R^1$, X, $R^2$, and L in Formulas II, III, and/or IV are as defined above for Formula I). Representative examples of useful alkenyl azlactones of Formula II include 4,4-dimethyl-2-vinyl-4H-oxazol-5-one (vinyldimethylazlactone, VDM), 2-isopropenyl-4H-oxazol-5-one, 4,4-dimethyl-2-isopropenyl-4H-oxazol-5-one, 2-vinyl-4,5-dihydro-[1,3]oxazin-6-one, 4,4-dimethyl-2-vinyl-4,5-dihydro-[1,3]oxazin-6-one, 4,5-dimethyl-2-vinyl-4,5-dihydro-[1,3]oxazin-6-one, and the like, and combinations thereof. Representative examples of ethylenically unsaturated isocyanates of general Formula III include 2-isocyanatoethyl (meth)acrylate (IEM or IEA), 3-isocyanatopropyl (meth)acrylate, 4-isocyanatocyclohexyl (meth)acrylate, and the like, and combinations thereof.

Representative examples of useful ligand functional group-containing compounds of general Formula IV include amino group-containing carboxylic, sulfonic, boronic, and phosphonic acids and combinations thereof. Useful amino carboxylic acids include α-amino acids (L-, D-, or DL-α-amino acids) such as glycine, alanine, valine, proline, serine, phenylalanine, histidine, tryptophan, asparagine, glutamine, N-benzylglycine, N-phenylglycine, sarcosine, and the like; β-aminoacids such as β-alanine, β-homoleucine, β-homoglutamine, β-homophenylalanine, and the like; other α,ω-aminoacids such as γ-aminobutyric acid, 6-aminohexanoic acid, 11-aminoundecanoic acid, peptides (such as diglycine, triglycine, tetraglycine, as well as other peptides containing a mixture of different aminoacids), and the like; and combinations thereof. Useful amino sulfonic acids include aminomethanesulfonic acid, 2-aminoethanesulfonic acid (taurine), 3-amino-1-propanesulfonic acid, 6-amino-1-hexanesulfonic acid, and the like, and combinations thereof. Useful aminoboronic acids include m-aminophenylboronic acid, p-aminophenylboronic acid, and the like, and combinations thereof. Useful aminophosphonic acids include 1-aminoethylphosphonic acid, 2-aminoethylphosphonic acid, 3-aminopropylphosphonic acid, and the like, and combinations thereof. Useful compounds of Formula IV containing more than one ligand functional group include aspartic acid, glutamic acid, α-aminoadipic acid, iminodiacetic acid, $N_\alpha,N_\alpha$-bis(carboxymethyl)lysine, cysteic acid, N-phosphonomethylglycine, and the like, and combinations thereof.

Representative examples of other useful ligand functional group-containing compounds of general Formula IV include compounds comprising a hydroxy group and an acidic group. Specific examples include glycolic acid, lactic acid, 6-hydroxyhexanoic acid, citric acid, 2-hydroxyethylsulfonic acid, 2-hydroxyethylphosphonic acid, and the like, and combinations thereof.

Representative examples of still other useful ligand functional group-containing compounds of general Formula IV include compounds comprising at least one amino or hydroxy group and at least one basic group such as a tertiary or quaternary amino group. Specific examples include 2-(dimethylamino)ethylamine, 3-(diethylamino)propylamine, 6-(dimethylamino)hexylamine, 2-aminoethyltrimethylammonium chloride, 3-aminopropyltrimethylammonium chloride, 2-(dimethylamino)ethanol, 3-(dimethylamino)-1-propanol, 6-(dimethylamino)-1-hexanol, 1-(2-aminoethyl)pyrrolidine, 2-[2-(dimethylamino)ethoxy]ethanol, histamine, 2-aminomethylpyridine, 4-aminomethylpyridine, 4-aminoethylpyridine, and the like, and combinations thereof.

Many of the above-described ligand functional group-containing compounds of general Formula IV are commercially available. Still other useful ligand functional group-containing compounds of general Formula IV can be prepared by common synthetic procedures. For example, various diamines or aminoalcohols can be reacted with one equivalent of a cyclic anhydride to produce an intermediate ligand functional group-containing compound comprising a carboxyl group and an amino or hydroxy group.

Useful monomers can also be prepared by the reaction of ligand functional group-containing compounds of general Formula IV with ethylenically unsaturated acyl halides (for example, (meth)acryloyl chloride). In addition, useful monomers can be prepared by reaction of hydroxy- or amine-containing (meth)acrylate or (meth)acrylamide monomers with a cyclic anhydride to produce carboxyl group-containing monomers.

Preferred monomers include monomers prepared from the reaction of alkenyl azlactones with aminocarboxylic acids, monomers prepared from the reaction of alkenyl azlactones with aminosulfonic acids, monomers prepared from the reaction of alkenyl azlactones with ligand functional group-containing compounds comprising a primary amino group and a tertiary or quaternary amino group, monomers prepared from the reaction of ethylenically unsaturated isocyanates with aminocarboxylic acids, monomers prepared from the reaction of ethylenically unsaturated isocyanates with aminosulfonic acids, monomers prepared from the reaction of ethylenically unsaturated isocyanates with ligand functional group-containing compounds comprising a primary or secondary amino group and a tertiary or quaternary amino group, and combinations thereof.

In preparing the article of the invention, the above-described monomers generally (and preferably) can be homopolymerized. A skilled artisan will recognize, however, that the monomers can be copolymerized with other monomers (hereinafter, termed "comonomers"; for example, comonomers having shorter spacer groups or comonomers comprising other types of ligands or even comonomers that are ligand-free) in order to adjust binding capacity and/or to achieve special properties, provided that the type and degree of binding capacity desired for a particular application can be achieved.

For example, the monomer(s) optionally can be copolymerized with one or more hydrophilic comonomer(s) comprising at least one alkenyl group (preferably, a (meth)acryloyl group) and a hydrophilic group (including poly(oxyalkylene) groups) in order to impart a degree of hydrophilicity to the porous substrate. Suitable hydrophilic comonomers include acrylamide, dimethylacrylamide, hydroxyethyl(meth)acrylate, hydroxypropyl(meth)acrylate, polyethyleneglycolmono(meth)acrylate, 2-hydroxyethylacrylamide, N-vinylpyrrolidone, and the like, and combinations thereof.

Optionally, the monomer(s) can be copolymerized with one or more (meth)acryloyl comonomer(s) containing at least two free radically polymerizable groups. Such multifunctional (meth)acryloyl comonomer(s) (including multifunctional (meth)acrylate(s) and (meth)acrylamide(s)) can be incorporated in a blend of polymerizable monomer(s) generally in only relatively small amounts (for example, from about 0.1 to about 5 percent by weight, based upon the total weight of monomer(s) and comonomer(s)) to impart a degree of branching and/or relatively light crosslinking to a resulting copolymer. Higher amounts can be used for certain applications, but it should be understood that the use of higher amounts may reduce binding capacity for a target biomaterial.

Useful multifunctional (meth)acryloyl comonomers include di(meth)acrylates, tri(meth)acrylates, tetra(meth)acrylates, multifunctional (meth)acrylamides, and the like, and combinations thereof. Such multifunctional (meth)acryloyl comonomers include ethyleneglycol di(meth)acrylate, 1,6-hexanediol di(meth)acrylate, poly(ethylene glycol)

di(meth)acrylates, polybutadiene di(meth)acrylate, polyurethane di(meth)acrylates, propoxylated glycerin tri(meth)acrylate, methylenebisacrylamide, ethylenebisacrylamide, hexamethylenebisacrylamide, diacryloylpiperazine, and the like, and combinations thereof.

Article Preparation and Use

Polymerization of the monomer(s) can be carried out by using known techniques. For example, the polymerization can be initiated with either a thermal initiator or a photoinitiator (preferably, a photoinitiator). Essentially any conventional free radical initiator can be used to generate the initial radical. Examples of suitable thermal initiators include peroxides such as benzoyl peroxide, dibenzoyl peroxide, dilauryl peroxide, cyclohexane peroxide, methyl ethyl ketone peroxide, hydroperoxides (for example, tert-butyl hydroperoxide and cumene hydroperoxide), dicyclohexyl peroxydicarbonate, t-butyl perbenzoate; 2,2,-azo-bis(isobutyronitrile); and the like; and combinations thereof. Examples of commercially available thermal initiators include initiators available from DuPont Specialty Chemical (Wilmington, Del.) under the VAZO trade designation including VAZO™ 67 (2,2'-azo-bis(2-methylbutyronitrile)), VAZO™ 64 (2,2'-azo-bis(isobutyronitrile)), and VAZO™ 52 (2,2'-azo-bis(2,2-dimethylvaleronitrile)), as well as Lucidol™ 70 (benzoylperoxide) available from Elf Atochem North America, Philadelphia, Pa.

Useful photoinitiators include benzoin ethers such as benzoin methyl ether and benzoin isopropyl ether; substituted acetophenones such as 2,2-dimethoxyacetophenone available as Irgacure™ 651 photoinitiator (Ciba Specialty Chemicals), 2,2 dimethoxy-2-phenyl-1-phenylethanone available as Esacure™ KB-1 photoinitiator (Sartomer Co.; West Chester, Pa.), 1-[4-(2-hydroxyethoxy)phenyl]-2-hydroxy-2-methyl-1-propan-1-one available as Irgacure™ 2959 (Ciba Specialty Chemicals), and dimethoxyhydroxyacetophenone; substituted α-ketols such as 2-methyl-2-hydroxy propiophenone; aromatic sulfonyl chlorides such as 2-naphthalene-sulfonyl chloride; photoactive oximes such as 1-phenyl-1,2-propanedione-2-(O-ethoxy-carbonyl)oxime; and the like; and combinations thereof. Particularly preferred among these are the substituted acetophenones (especially 1-[4-(2-hydroxyethoxy)phenyl]-2-hydroxy-2-methyl-1-propan-1-one, Irgacure™ 2959, due to its water solubility). A particularly useful polymerizable photoinitiator is a 1:1 adduct of 2-vinyl-4,4-dimethylazlactone and Irgacure™ 2959, which can be prepared essentially as described in Example 1 of U.S. Pat. No. 5,506,279 (Babu et al.), the description of which preparation is incorporated herein by reference.

Other useful photoinitiators include hydrogen-abstracting (Type II) photoinitiators such as benzophenone, 4-(3-sulfopropyloxy)benzophenone sodium salt, Michler's ketone, benzil, anthraquinone, 5,12-naphthacenequinone, aceanthracenequinone, benz(A)anthracene-7,12-dione, 1,4-chrysenequinone, 6,13-pentacenequinone, 5,7,12,14-pentacenetetrone, 9-fluorenone, anthrone, xanthone, thioxanthone, 2-(3-sulfopropyloxy)thioxanthen-9-one, acridone, dibenzosuberone, acetophenone, chromone, and the like, and combinations thereof.

The initiator can be used in an amount effective to initiate free radical polymerization of the monomer(s). Such amount will vary depending upon, for example, the type of initiator and polymerization conditions utilized. The initiator generally can be used in amounts ranging from about 0.01 part by weight to about 5 parts by weight, based upon 100 parts total monomer.

The polymerization solvent can be essentially any solvent that can substantially dissolve (or, in the case of emulsion or suspension polymerizations, disperse or suspend) the monomer(s) (and comonomer(s), if used). In many embodiments, the solvent can be water or a water/water-miscible organic solvent mixture. The ratio of water to organic solvent can vary widely, depending upon monomer solubility. With some monomers, the ratio typically can be greater than 1:1 (volume/volume) water to organic solvent (preferably, greater than 5:1; more preferably, greater than 7:1). With other monomers, a higher proportion of organic solvent (even up to 100 percent) can be preferred (with some alcohols especially).

Any such water-miscible organic solvent preferably has no groups that would retard polymerization. In some embodiments, the water-miscible solvents can be protic group-containing organic liquids such as the lower alcohols having 1 to 4 carbon atoms, lower glycols having 2 to 6 carbon atoms, and lower glycol ethers having 3 to 6 carbon atoms and 1 to 2 ether linkages. In some embodiments, higher glycols such as poly(ethylene glycol) can be used. Specific examples include methanol, ethanol, isopropanol, n-butanol, t-butyl alcohol, ethylene glycol, methoxyethanol, ethoxyethanol, propoxyethanol, butoxyethanol, methyl carbitol, ethyl carbitol, and the like, and combinations thereof.

In other embodiments, non-protic water-miscible organic solvents can be used. Such solvents include aliphatic esters (for example, methoxyethyl acetate, ethoxyethyl acetate, propoxyethyl acetate, butoxyethyl acetate, and triethyl phosphate), ketones (for example, acetone, methyl ethyl ketone, and methyl propyl ketone), and sulfoxides (for example, dimethyl sulfoxide).

The monomer concentration in the polymerization solvent can vary, depending upon a number of factors including, but not limited to, the nature of the monomer or monomers, the extent of polymerization desired, the reactivity of the monomer(s), and the solvent used. Typically, the monomer concentration can range from about 0.1 weight percent (wt %) to about 60 wt % (preferably, from about 1 wt % to about 40 wt %; more preferably, from about 5 wt % to about 30 wt %), based upon the total weight of monomer and solvent.

An aqueous monomer mixture optionally can be formulated with relatively higher levels of multifunctional (crosslinking) monomers or comonomers (for example, from about 5 percent (%) by weight up to about 90% by weight, based upon the total weight of monomer(s) and comonomer(s)) and polymerized as a suspension or dispersion in a nonpolar, immiscible organic solvent, optionally in the presence of added porogen(s), to produce crosslinked, porous particles comprising the instant monomer(s). Such methods are well known and are described, for example, in U.S. Pat. No. 7,098,253 (Rasmussen et al.), U.S. Pat. No. 7,674,835 (Rasmussen et al.), U.S. Pat. No. 7,647,836 (Rasmussen et al.), and U.S. Pat. No. 7,683,100 (Rasmussen et al.), the descriptions of which methods are incorporated herein by reference.

If desired, the polymerization can be carried out in the presence of a porous substrate, so as to form an article comprising a porous substrate bearing the resulting polymer. For example, an imbibing or coating solution comprising the monomer(s), any comonomer(s), initiator(s), and solvent(s) can be imbibed by or coated (or otherwise deposited) on a porous substrate. The porous substrate can be in essentially any form such as particles, fibers, films, webs, membranes, sponges, or sheets. Suitable porous substrates can be organic, inorganic, or a combination thereof (preferably, organic; more preferably, polymeric). Suitable porous substrates include porous particles, porous membranes, porous nonwoven webs, porous woven webs, porous sponges, porous fibers, and the like, and combinations thereof. Preferred porous substrates include porous membranes (more preferably, porous polymeric membranes; most preferably, porous polyamide membranes) and combinations thereof.

For example, the porous substrate can be formed from any suitable thermoplastic polymeric material. Suitable polymeric materials include polyolefins, poly(isoprenes), poly(butadienes), fluorinated polymers, chlorinated polymers, polyamides, polyimides, polyethers, poly(ether sulfones), poly(sulfones), poly(vinyl acetates), polyesters such as poly(lactic acid), copolymers of vinyl acetate such as poly(ethylene)-co-poly(vinyl alcohol), poly(phosphazenes), poly(vinyl esters), poly(vinyl ethers), poly(vinyl alcohols), poly(carbonates), and the like, and combinations thereof.

In some embodiments, the thermoplastic polymer can be surface treated, such as by plasma discharge or by use of a primer, to provide suitable functionality to the surface of the porous substrate. Surface treatment can provide functional groups such as hydroxy groups that can improve wetting by the monomer solution. One such useful plasma treatment is described in U.S. Pat. No. 7,125,603 (David et al.).

Suitable polyolefins include poly(ethylene), poly(propylene), poly(l-butene), copolymers of ethylene and propylene, alpha olefin copolymers (such as copolymers of ethylene or propylene with 1-butene, 1-hexene, 1-octene, and 1-decene), poly(ethylene-co-1-butene), poly(ethylene-co-1-butene-co-1-hexene), and the like, and combinations thereof.

Suitable fluorinated polymers include poly(vinyl fluoride), poly(vinylidene fluoride), copolymers of vinylidene fluoride (such as poly(vinylidene fluoride-co-hexafluoropropylene)), copolymers of chlorotrifluoroethylene (such as poly(ethylene-co-chlorotrifluoroethylene)), and the like, and combinations thereof.

Suitable polyamides include poly(iminoadipolyliminohexamethylene), poly(iminoadipolyliminodecamethylene), polycaprolactam, and the like, and combinations thereof. Suitable polyimides include poly(pyromellitimide), and the like, and combinations thereof.

Suitable poly(ether sulfones) include poly(diphenylether sulfone), poly(diphenylsulfone-co-diphenylene oxide sulfone), and the like, and combinations thereof.

Suitable copolymers of vinyl acetate include poly(ethylene-co-vinyl acetate), such copolymers in which at least some of the acetate groups have been hydrolyzed to afford various poly(vinyl alcohols), and the like, and combinations thereof.

A preferred porous substrate is a microporous membrane such as a thermally-induced phase separation (TIPS) membrane. TIPS membranes are often prepared by forming a solution of a thermoplastic material and a second material above the melting point of the thermoplastic material. Upon cooling, the thermoplastic material crystallizes and phase separates from the second material. The crystallized material is often stretched. The second material is optionally removed either before or after stretching. Microporous membranes are further described in U.S. Pat. No. 4,539,256 (Shipman); U.S. Pat. No. 4,726,989 (Mrozinski); U.S. Pat. No. 4,867,881 (Kinzer); U.S. Pat. No. 5,120,594 (Mrozinski); U.S. Pat. No. 5,260,360 (Mrozinski); and U.S. Pat. No. 5,962,544 (Waller, Jr.). Some exemplary TIPS membranes comprise poly(vinylidene fluoride) (PVDF), polyolefins such as poly(ethylene) or poly(propylene), vinyl-containing polymers or copolymers such as ethylene-vinyl alcohol copolymers and butadiene-containing polymers or copolymers, and acrylate-containing polymers or copolymers. For some applications, a TIPS membrane comprising PVDF can be particularly desirable. TIPS membranes comprising PVDF are further described in U.S. Pat. No. 7,338,692 (Smith et al.).

In many embodiments, the porous substrate can have an average pore size that is typically greater than about 0.2 micrometers in order to minimize size exclusion separations, minimize diffusion constraints, and maximize surface area and separation based on binding of a target biomaterial. Generally, the pore size can be in the range of 0.1 to 10 micrometers (preferably, 0.5 to 3 micrometers; most preferably, 0.8 to 2 micrometers when used for binding of viruses and/or proteins). The efficiency of binding other target biomaterials can confer different optimal ranges.

In an exemplary embodiment, the porous substrate can comprise a nylon microporous film or sheet (for example, a microporous membrane), such as those described in U.S. Pat. No. 6,056,529 (Meyering et al.), U.S. Pat. No. 6,267,916 (Meyering et al.), U.S. Pat. No. 6,413,070 (Meyering et al.), U.S. Pat. No. 6,776,940 (Meyering et al.), U.S. Pat. No. 3,876,738 (Marinaccio et al.), U.S. Pat. No. 3,928,517 (Knight et al.), U.S. Pat. No. 4,707,265 (Barnes, Jr. et al.), and U.S. Pat. No. 5,458,782 (Hou et al.).

In other embodiments, the porous substrate can be a nonwoven web, which can include nonwoven webs manufactured by any of the commonly known processes for producing nonwoven webs. As used herein, the term "nonwoven web" refers to a fabric that has a structure of individual fibers or filaments that are randomly and/or unidirectionally interlaid in a mat-like fashion.

For example, the fibrous nonwoven web can be made by wet laid, carded, air laid, spunlaced, spunbonding, or melt-blowing techniques, or combinations thereof. Spunbonded fibers are typically small diameter fibers that are formed by extruding molten thermoplastic polymer as filaments from a plurality of fine, usually circular capillaries of a spinneret, with the diameter of the extruded fibers being rapidly reduced. Meltblown fibers are typically formed by extruding molten thermoplastic material through a plurality of fine, usually circular, die capillaries as molten threads or filaments into a high velocity, usually heated gas (for example, air) stream, which attenuates the filaments of molten thermoplastic material to reduce their diameter. Thereafter, the meltblown fibers are carried by the high velocity gas stream and are deposited on a collecting surface to form a web of randomly-dispersed, meltblown fibers. Any of the nonwoven webs can be made from a single type of fiber or from two or more fibers that differ in the type of thermoplastic polymer and/or thickness.

Further details of manufacturing methods of useful nonwoven webs have been described by Wente in "Superfine Thermoplastic Fibers," 48 Indus. Eng. Chem. 1342 (1956) and by Wente et al. in "Manufacture Of Superfine Organic Fibers," Naval Research Laboratories Report No. 4364 (1954).

Following polymerization, washing, and drying, typical total weight gains by the porous substrate generally can be in the range of about 5 percent (%) to about 30% (preferably, in the range of about 10% to about 25%; more preferably, in the range of about 12% to about 20%). Polymerization of the monomer(s) in the presence of a porous substrate can produce a polymer-bearing porous substrate. The polymer can be in the form of a coating or, in preferred embodiments, the polymer can be grafted (covalently bonded) to the surface of the porous substrate. (If desired, the polymerization can be carried out separately and the resulting polymer then coated (optionally in the presence of suitable crosslinker) or grafted or otherwise applied to the porous substrate, but this is generally less preferred.)

In an exemplary method, the monomer(s) can be free radically polymerized and grafted to the surface of a porous substrate in the presence of a Type II photoinitiator, as described in International Patent Application No. US2013/042330 (3M Innovative Properties Co.), the description of which method is incorporated herein by reference. Alternatively, the monomer(s) can be free radically polymerized and grafted to a porous substrate comprising a crosslinked copolymer layer, the copolymer comprising photoinitiator-containing monomer units, as described in U.S. Provisional Patent Application No. 61/706,288 (Rasmussen et al.), the description of which method is incorporated herein by reference. In addition, the monomer(s) can be free radically polymerized and grafted to a porous substrate comprising a crosslinked polymer primer layer, as described in U.S. Patent Application Publication No. 2012/0252091 A1 (Rasmussen et al.), the description of which method is incorporated herein by reference. In yet another exemplary method, the monomer(s) can be free radically polymerized and grafted to a porous particle, as described in U.S. Patent Application Publication No. 2011/0100916 A1 (Shannon et al.), the description of which method is incorporated herein by reference.

The coated or grafted polymer (which is ligand-functional polymer due to the presence of the ligand functional groups of the monomer(s)) can alter the original nature of the porous substrate. The resulting polymer-bearing porous substrates (ligand-functionalized porous substrates) can retain many of the advantages of the original porous substrate (for example, mechanical and thermal stability, porosity, and so forth) but can also exhibit enhanced affinity for biomaterials such as viruses, proteins, and the like. Porous substrates bearing the ligand-functional polymer can be particularly useful as filter media for the selective binding and removal of target biomaterials or biological species (including relatively neutral or charged biomaterials such as viruses and other microorganisms, acidic carbohydrates, proteins, nucleic acids, endotoxins, bacteria, cells, cellular debris, and the like) from biological samples. Articles comprising the polymer-bearing porous substrates can further comprise conventional components such as housings, holders, adapters, and the like, and combinations thereof.

If desired, efficiency of binding and capture of biomaterials can be improved by using a plurality of stacked or layered, functionalized porous substrates (for example, functionalized porous membranes) as a filter element. Thus, a filter element can comprise one or more layers of functionalized porous substrate. The individual layers of the filter element can be the same or different. The layers can vary in porosity, degree of grafting, and so forth. The filter element can further comprise an upstream prefilter layer and/or a downstream support layer. The individual layers can be planar or pleated, as desired.

Examples of suitable prefilter and support layer materials include any suitable porous membranes of polypropylene, polyester, polyamide, resin-bonded or binder-free fibers (for example, glass fibers), and other synthetics (woven and nonwoven fleece structures); sintered materials such as polyolefins, metals, and ceramics; yarns; special filter papers (for example, mixtures of fibers, cellulose, polyolefins, and binders); polymer membranes; and the like; and combinations thereof.

Useful articles for biomaterial capture or filtration applications include a filter cartridge comprising one or more of the above-described filter elements, a filter assembly comprising one or more of the above-described filter elements and a filter housing, and the like. The articles can be used in carrying out a method of capture or removal of a target biomaterial or biological species comprising (a) providing at least one article comprising at least one above-described filter element; and (b) allowing a moving biological solution containing a target biomaterial to impinge upon the upstream surface of the filter element for a time sufficient to effect binding of the target biomaterial.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

Materials

Unless otherwise noted, all parts, percentages, ratios, etc., in the examples and in the remainder of the specification are by weight. Unless otherwise noted, all chemicals were obtained from, or are available from, chemical suppliers such as Sigma-Aldrich Chemical Company, St. Louis, Mo.

VDM—vinyldimethylazlactone, SNPE, Inc, Princeton, N.J.

MBA—methylenebisacrylamide, Sigma-Aldrich, Milwaukee, Wis.

PEG200MA—polyethyleneglycol monomethacrylate, molecular weight (MW) about 200, Polysciences, Warrington, Pa.

PEG400MA—polyethyleneglycol monomethacrylate, MW about 400, Polysciences, Warrington, Pa.

IEM—2-isocyanatoethyl methacrylate, Showa Denko KK, Kanagawa, Japan

S-BP—4-(3-sulfopropyloxy)benzophenone, sodium salt (which is a water-soluble benzophenone), prepared essentially as described in Japanese Patent No. 47040913 Teijin Ltd.)

Test Methods

Static Lysozyme Capacity Method for Functionalized Substrates

Functionalized substrates prepared as described in the Examples below were analyzed for static binding capacity by incubating one disk of the substrate in a solution of a test analyte overnight. The disk was prepared by die-punching a 24-mm diameter disk from a sheet of the substrate. Each disk was placed in a 5 mL centrifuge tube with 4.5 mL of chicken egg white lysozyme (Sigma-Aldrich, St. Louis, Mo.) challenge solution at a concentration of about 5.0 mg/mL in 10 mM MOPS (4-morpholinopropanesulfonic acid; Sigma-Aldrich, St. Louis, Mo.) buffer at pH 7.5. The tubes were capped and tumbled overnight (typically 14 hours) on a rotating mixer (BARNSTEAD/THERMOLYN LABQUAKE™ Tube Shaker, obtained from VWR International, Eagan, Minn.). The resulting supernatant solutions were analyzed using an ultraviolet-visible (UV-VIS) spectrometer (AGILENT™ 8453, Agilent Technologies, Santa Clara, Calif.) at 280 nanometers (nm) (with background correction applied at 325 nm). The static binding capacity for each substrate was determined by comparison to the absorbance of the starting lysozyme solution, and results are reported in mg/mL (mg of protein bound/mL of membrane volume) as the average of three replicates.

Static BSA Capacity Method for Functionalized Substrates

Functionalized substrates prepared as described in the Examples below were analyzed for static binding capacity by incubating one disk of the substrate in a solution of a test analyte overnight. The disk was prepared by die-punching a 24-mm diameter disk from a sheet of the substrate. Each disk was placed in a 5 mL centrifuge tube with 4.5 mL of BSA (bovine serum albumin) challenge solution (Catalog # A-7906; Sigma-Aldrich, St. Louis, Mo.) at a concentration of about 3.0 mg/ml in 25 millimolar TRIS (tris(hydroxymethyl)aminomethane; Sigma-Aldrich, St. Louis, Mo.) buffer, pH 8.0. The tubes were capped and tumbled overnight (typically 14 hours) on a rotating mixer (BARNSTEAD/THERMOLYN LABQUAKE™ Tube Shaker, obtained from VWR International, Eagan, Minn.). The resulting supernatant solutions were analyzed using a UV-VIS spectrometer (AGILENT™ 8453, Agilent Technologies, Santa Clara, Calif.) at 279 nm (with background correction applied at 325 nm). The static binding capacity for each substrate was determined by comparison to the absorbance of the starting BSA solution, and results are reported in mg/mL as the average of three replicates.

Static IgG Capacity Method for Functionalized Substrates (IgG Method 1)

Functionalized substrates prepared as described in the Examples below were analyzed for static binding capacity by incubating one disk of the substrate in a solution of a test analyte overnight. The disk was prepared by die-punching a 24-mm diameter disk from a sheet of the substrate. Each disk was placed in a 5 mL centrifuge tube with 4.5 mL of human IgG (Sigma-Aldrich, St. Louis, Mo.) challenge solution at a concentration of about 5.5 mg/mL in 50 mM HEPES (N-(2-hydroxyethyl)piperazine-N'-(4-butanesulfonic acid); Sigma-Aldrich, St. Louis, Mo.) buffer at pH 7.0. The tubes were capped and tumbled overnight (typically 14 hours) on a rotating mixer (BARNSTEAD/THERMOLYN LABQUAKE™ Tube Shaker, obtained from VWR International, Eagan, Minn.). The resulting supernate was poured off, and the disks were washed with HEPES buffer (4.5 mL) for 30 minutes on the rotating mixer. The resulting supernate was poured off, and then the wash procedure was repeated. The resulting supernate was again poured off and was replaced by elution buffer (4.5 mL, 50 mM HEPES, 1 M NaCl, pH 7.0). The tubes were tumbled on the rotating mixer for 30 minutes, then the resulting supernate was analyzed using a UV-VIS spectrometer (AGILENT™ 8453, Agilent Technologies, Santa Clara, Calif.) at 280 nm (with background correction applied at 325 nm). The static binding capacity for each substrate was determined from the measured IgG concentration in the supernate, and results are reported in mg/mL as the average of three replicates.

Static IgG Capacity Method for Functionalized Substrates (IgG Method 2)

Functionalized substrates prepared as described in the Examples below were analyzed for static binding capacity by incubating one disk of the substrate in a solution of a test analyte overnight. The disk was prepared by die-punching a 24-mm diameter disk from a sheet of the substrate. Each disk was placed in a 5 mL centrifuge tube with 4.5 mL of human IgG (Equitech Bio, Kerrville, Tex.) challenge solution at a concentration of about 2.0 mg/mL in 50 mM acetic acid/sodium acetate buffer (Sigma-Aldrich, St. Louis, Mo.) with 40 mM NaCl at pH 4.5. The tubes were capped and tumbled overnight (typically 14 hours) on a rotating mixer (BARNSTEAD/THERMOLYN LABQUAKE™ Tube Shaker, obtained from VWR International, Eagan, Minn.). The supernatant solutions were analyzed using a UV-VIS spectrometer (AGILENT™ 8453, Agilent Technologies, Santa Clara, Calif.) at 280 nm (with background correction applied at 325 nm). The static binding capacity for each substrate was determined by comparison to the absorbance of the starting IgG solution, and results are reported in mg/mL as the average of three replicates.

Graft Density and Ligand Efficiency

Nylon membrane substrates (nylon 66 membrane, single reinforced layer nylon three-zone membrane, nominal pore size 1.8 μm, #080ZN, obtained from 3M Purification, Inc., Meridan, Conn.) were equilibrated for a minimum of 18 hours in a low humidity chamber (Sanpia Dry Keeper, Sanplatec Corporation, available from VWR International) at a relative humidity (RH) of 20-25 percent (%), prior to being grafted. The substrates were removed from the low humidity chamber, weighed immediately, and then subjected to a free radical grafting reaction as described below for a variety of ligand functional group-containing monomers. Following a washing and drying process (as described below), the substrates were again equilibrated in the low humidity chamber for a minimum of 18 hours, were removed from the chamber, and were reweighed immediately to obtain a measurement of mass gain during the grafting reaction. The mass gain was subsequently utilized to estimate the number of millimoles of monomer grafted to the substrate by dividing the mass gain by the molecular weight of the monomer. Graft density was then normalized by dividing by the original mass of the substrate and expressed as millimoles of monomer grafted per gram of substrate (mmol/g). Ligand efficiency was expressed as the quotient of lysozyme static capacity to graft density (capacity/mmol/g).

$^1$H NMR Analysis

Proton nuclear magnetic resonance CH NMR) analysis was carried out using a nuclear magnetic resonance (NMR) spectrometer (BRUKER™ A500, obtained from Bruker Corp., Billerica, Mass.) in the solvents listed in each example or table entry below. Splitting patterns in the $^1$H-NMR data are designated using the following abbreviations: s=singlet; br. s=broad singlet; 2s=two singlets; d=doublet; dd=doublet of doublets; t=triplet; q=quartet; p=pentet; and m=multiplet.

Monomer Preparative Methods

Preparation of Ligand Functional Group-Containing Monomers

Preparations of a variety of representative examples of ligand functional group-containing monomers are described below. Chemical structures are provided for several of the monomers. In some cases, a numbering scheme is also provided to illustrate the counting of spacer group atoms.

Preparative Example 1

Preparation of the VDM Adduct of Glycine

Glycine (1.50 g, 0.02 mol) was charged to a 100 mL round bottom flask. Sodium hydroxide solution (1 N, 20 mL) was added to the flask. The resulting mixture was stirred magnetically until dissolved and then cooled in an ice-water bath with continued stirring for 15 minutes. VDM (2.78 g, 2.5 mL, 0.02 mol) was added to the cooled mixture by syringe. The resulting mixture was stirred for 30 minutes with ice-bath cooling and then allowed to warm to room temperature over 30 minutes. $^1$H-NMR (D$_2$O) δ 1.38 (s, 6H), 3.60 (s, 2H), 5.63 (d, 1H), 6.0-6.2 (m, 2H) indicated complete conversion to the desired acrylamide monomer as the sodium salt.

Preparative Examples 2-6

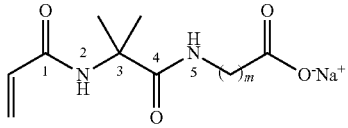

By procedures essentially analogous to that of Preparative Example 1 (wherein m=1), additional monomers (having spacer groups of chain length=5+m, wherein m varies, and having two hydrogen bond donors) were prepared from the following aminoacids:

Prep. Ex. 2

β-alanine (m=2; number of spacer atoms=7): $^1$H-NMR (D$_2$O) δ 1.32 (s, 6H), 2.23 (t, 2H), 3.24 (t, 2H), 5.63 (m, 1H), 6.0-6.2 (m, 2H)

Prep. Ex. 3

γ-aminobutyric acid (m=3; number of spacer atoms=8): $^1$H-NMR (D$_2$O) δ 1.34 (s, 6H), 1.59 (p, 2H), 2.04 (t, 2H), 3.05 (t, 2H), 5.62 (d, 1H), 6.0-6.2 (m, 2H)

Prep. Ex. 4

6-aminocaproic acid (m=5; number of spacer atoms=10): $^1$H-NMR (D$_2$O) δ 1.14 (m, 2H), 1.34 (s and m, 8H), 1.41 (m, 2H), 2.02 (t, 2H), 3.03 (t, 2H), 5.62 (d, 1H), 6.0-6.2 (m, 2H)

Prep. Ex. 5

5-aminovaleric acid (m=4; number of spacer atoms=9): $^1$H-NMR (D$_2$O) δ 1.33 (s and m, 10H), 2.04 (t, 2H), 3.05 (t, 2H), 5.63 (d, 1H), 6.0-6.2 (m, 2H)

Prep. Ex. 6

11-aminoundecanoic acid (m=9; number of spacer atoms=14): $^1$H-NMR (CD$_3$OD) δ 1.26 (br. s, 12H), 1.45 (s and m, 8H), 1.55 (m, 2H), 2.12 (t, 2H), 3.13 (t, 2H), 5.66 (d, 1H), 6.15-6.35 (m, 2H)

Preparative Examples 7-11

By procedures essentially analogous to that of Preparative Example 1, additional monomers (having spacer groups with the numbered chain lengths shown in the following structures and/or otherwise provided below) were prepared from the following aminoacids:

Prep. Ex. 7 diglycine (number of spacer atoms=9, and having three hydrogen bond donors): $^1$H-NMR (D$_2$O) δ 1.37 (s, 6H), 3.66 (s, 2H), 3.79 (s, 2H), 5.66 (d, 1H), 6.12 (m, 2H)

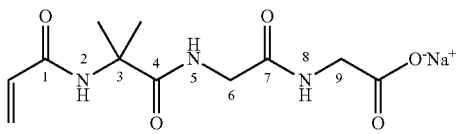

Prep. Ex. 8 triglycine (number of spacer atoms=12, and having four hydrogen bond donors): $^1$H-NMR (D$_2$O) δ 1.37 (s, 6H), 3.64 (s, 2H), 3.82 (s, 2H), 3.88 (s, 2H) 5.66 (d, 1H), 6.11 (m, 2H)

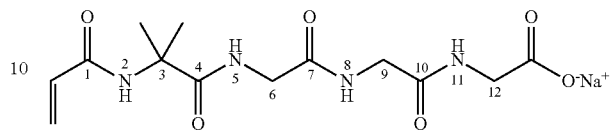

Prep. Ex. 9

L-phenylalanine (number of spacer atoms=6, and having two hydrogen bond donors): $^1$H-NMR (D$_2$O) δ 1.26 (s, 6H), 2.89 (m, 1H), 2.95 (m, 1H), 4.30 (m, 1H), 5.62 (d, 1H), 6.00-6.10 (m, 2H), 7.07-7.20 (m, 5H)

Prep. Ex. 10

L-tryptophan (number of spacer atoms=6, and having two hydrogen bond donors): $^1$H-NMR (D$_2$O) δ 1.12 and 1.14 (2s, 6H), 3.03 (m, 1H), 3.14 (m, 1H), 4.34 (m, 1H), 5.52 (m, 1H), 5.93 (m, 2H), 6.90-7.01 (m, 3H), 7.22 (d, 1H), 7.48 (d, 1H)

Prep. Ex. 11

L-histidine (number of spacer atoms=6, and having two hydrogen bond donors): $^1$H-NMR (D$_2$O) δ 1.23 and 1.25 (2s, 6H), 2.76 (dd, 1H), 2.91 (dd, 1H), 4.16 (m, 1H), 5.55 (m, 1H), 6.00 (m, 2H), 6.68 (s, 1H), 7.43 (s, 1H)

Preparative Examples 12-15

Preparation of IEM Adducts of Aminoacids

Monomers (having spacer groups of chain length=7+m, wherein m varies) were prepared by essentially the procedure described in Preparative Examples 1-4, except that VDM was replaced by IEM (3.1 g, 0.02 mol). At the end of each reaction, a small amount of colorless precipitate was filtered from the reaction mixture prior to use. $^1$H-NMR verified the formation of the desired adducts as the sodium salts.

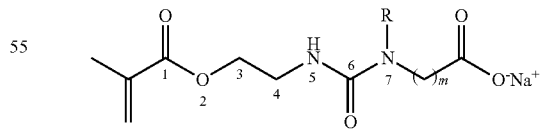

Prep. Ex. 12 glycine (m=1; number of spacer atoms=8; R=H; having two hydrogen bond donors): $^1$H-NMR (D$_2$O) δ 1.79 (s, 3H), 3.33 (m, 2H), 3.54 (s, 2H), 4.09 (m, 2H), 5.59 (s, 1H), 5.99 (s, 1H)

Prep. Ex. 13

β-alanine (m=2; number of spacer atoms=9; R=H; having two hydrogen bond donors): $^1$H-NMR (D$_2$O) δ 1.78 (s, 3H), 2.22 (t, 2H), 3.16 (t, 2H), 3.30 (t, 2H), 4.07 (t, 2H), 5.58 (s, 1H), 5.99 (s, 1H)

Prep. Ex. 14

γ-aminobutyric acid (m=3; number of spacer atoms=10; R=H; having two hydrogen bond donors): $^1$H-NMR (D$_2$O) δ 1.57 (t, 2H), 1.78 (s, 3H), 2.05 (t, 2H), 2.95 (m, 2H), 3.31 (m, 2H), 4.08 (m, 2H), 5.58 (s 1H), 5.99 (s, 1H)

Prep. Ex. 15

6-aminocaproic acid (m=5; number of spacer atoms=12; R=H; having two hydrogen bond donors): $^1$H-NMR (D$_2$O) δ 1.15 (m, 2H), 1.32 (m, 2H), 1.40 (m, 2H), 1.77 (s, 3H), 2.02 (m, 2H), 2.93 (m, 2H), 3.30 (m, 2H), 4.07 (m, 2H), 5.58 (s, 1H), 5.99 (s, 1H)

Preparative Examples 16-21

Preparation of IEM Adducts of Aminoacids

Monomers (having spacer groups with the chain lengths provided below) were prepared by essentially the procedure described in Preparative Examples 1-4, except that VDM was replaced by IEM (3.1 g, 0.02 mol). At the end of each reaction, a small amount of colorless precipitate was filtered from the reaction mixture prior to use. $^1$H-NMR verified the formation of the desired adducts as the sodium salts.

Prep. Ex. 16 diglycine (number of spacer atoms=11; R=H; having three hydrogen bond donors): $^1$H-NMR (D$_2$O) δ 1.79 (s, 3H) 3.34 (t, 2H), 3.65 (s, 2H), 3.72 (s, 2H), 4.11 (t, 2H), 5.59 (s, 1H), 6.00 (s, 1H)

Prep. Ex. 17 triglycine (number of spacer atoms=14; R=H; having four hydrogen bond donors): $^1$H-NMR (D$_2$O) δ 1.79 (s, 3H) 3.34 (t, 2H), 3.65 (s, 2H), 3.75 (s, 2H), 3.86 (s, 2H), 4.11 (t, 2H), 5.59 (s, 1H), 6.00 (s, 1H)

Prep. Ex. 18 sarcosine (number of spacer atoms=8; R=CH$_3$; having one hydrogen bond donor): $^1$H-NMR (D$_2$O) δ 1.79 (s, 3H), 2.75 (s, 3H), 3.35 (t, 2H), 3.69 (s, 2H), 4.11 (t, 2H), 5.59 (d, 1H), 6.00 (d, 1H)

Prep. Ex. 19

L-phenylalanine (number of spacer atoms=8; R=H; having two hydrogen bond donors): $^1$H-NMR (D$_2$O) δ 1.74 (br. s, 3H), 2.73 (m, 1H), 2.99 (m, 1H), 3.13 (m, 1H), 3.26 (m 1H), 3.90 (m, 2H), 4.17 (m, 1H), 5.54 (m, 1H), 5.95 (m, 1H), 7.09 and 7.15 (m, 5H)

Prep. Ex. 20

L-tryptophan (number of spacer atoms=8; R=H; having two hydrogen bond donors): $^1$H-NMR (D$_2$O) δ 1.51 (s, 3H), 2.93 (m, 2H), 3.10 (m, 2H), 3.67 (br. s, 2H), 4.27 (br. s, 1H), 5.24 (br. s, 1H), 5.73 (br. s, 1H), 6.79 (m, 1H), 6.81 (m, 1H), 6.85 (s, 1H), 7.11 (m, 1H), 7.37 (m, 1H)

Prep. Ex. 21

L-histidine (number of spacer atoms=8; R=H; having two hydrogen bond donors): $^1$H-NMR (D$_2$O) δ 1.64 (s, 3H), 2.69 (m, 1H), 2.86 (m, 1H), 3.14 (m, 1H), 3.22 (m, 1H), 3.91 (m, 2H), 4.08 (m, 1H), 5.44 (m, 1H), 5.85 (s, 1H), 6.69 (s, 1H), 7.46 (s, 1H)

Preparative Example 22

Preparation of the Monomethacryloyloxyethyl Ester of Glutaric Acid

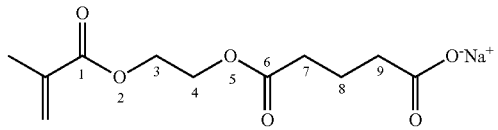

Glutaric anhydride (3.50 g, 0.03 mol) was charged to a 100 mL round bottom flask, and dichloromethane (50 mL) was added to the flask. The resulting mixture was stirred magnetically until the anhydride dissolved, and then 2-hydroxyethyl methacrylate (3.99 g, 0.03 mol) was added to the flask. The resulting mixture was stirred for 15 minutes and then cooled in an ice-water bath to 0° C. Triethylamine (3.1 g, 4.3 mL, 0.03 mol) was added by syringe to the stirring mixture, then 4-dimethylaminopyridine (0.06 g, 0.03 mol) was also added. The resulting mixture was stirred for 2 hours with ice-bath cooling and was then allowed to warm to room temperature over 30 minutes. The resulting mixture was stirred for an additional 12 hours at room temperature.

Excess solvent was then removed from the mixture by rotary evaporation. The resulting residue was dissolved in diethyl ether, and product was extracted from the resulting solution into a saturated sodium bicarbonate (3×50 mL) phase. The final pH of the phase (basic solution) was adjusted to 2 by adding 1N HCl. The product was extracted from the resulting acidic aqueous phase into diethyl ether (3×100 mL). The resulting combined diethyl ether extract was then washed with brine and dried over Na$_2$SO$_4$. Solids were removed from the extract by filtration, and solvent was then removed by rotary evaporation to yield the product as a colorless liquid.

$^1$H-NMR (CDCl$_3$) δ 1.93 (t, 3H), 1.95 (m, 2H), 2.45 (m, 4H), 4.34 (m, 4H), 5.59 (m, 1H), 6.12 (m, 1H) indicated complete conversion to the desired monomer product (having 9 spacer atoms, as shown in the structure above, but no hydrogen bond donors). A solution was prepared by dissolving the monomer (3.15 g, 0.013 mol) in 1 N sodium hydroxide (12.9 mL).

Preparative Example 23

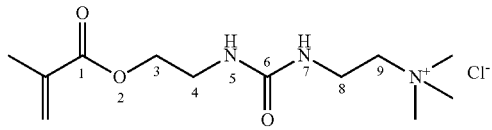 [SMILES: C=C(C)C(=O)OCCNC(=O)NCC[N+](C)(C)C ; [Cl-]]

2-Aminoethyltrimethylammonium chloride (Sigma-Aldrich, St. Louis, Mo.; 5.1 g, 0.029 mol) was charged to a 100 mL round bottom flask and dissolved in sodium hydroxide solution (1N, 29 mL) with magnetic stirring. The resulting solution was cooled in an ice-water bath for 10 minutes, and then IEM (4.51 g, 0.029 mol) was added to the solution. Stirring was continued for 2 hours, and then a small amount of colorless precipitate was filtered. NMR analysis verified the formation of the expected methacrylate adduct (having 9 spacer atoms, as shown in the structure above, and two hydrogen bond donors). $^1$H-NMR (D$_2$O) δ 1.80 (s, 3H), 3.05 (s, 9H), 3.33 (m, 4H), 3.50 (m, 2H), 4.12 (t, 2H), 5.61 (s, 1H), 6.01 (s, 1H).

Preparative Example 24

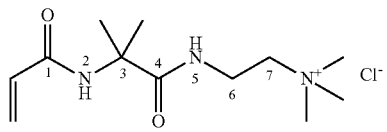 [SMILES: C=CC(=O)NC(C)(C)C(=O)NCC[N+](C)(C)C ; [Cl-]]

The procedure of Preparative Example 23 was essentially repeated, except that VDM (4.03 g, 0.029 mol) was used instead of IEM (to form monomer having 7 spacer atoms, as shown in the structure above, and two hydrogen bond donors). $^1$H-NMR (D$_2$O) δ 1.30 (s, 6H), 3.01 (s, 9H), 3.30 (m, 2H), 3.52 (m, 2H) 5.60 (m, 1H), 6.01 (m, 1H), 6.13 (m, 1H).

Preparative Examples 25-33

Monomers (having spacer groups with the numbered chain lengths shown in the following structures and/or otherwise provided below) were prepared from various aminoacids by essentially the procedures described in Preparative Examples 1 and 12, using either VDM or IEM, respectively. Preparative Examples 25, 27, 29, 31, and 33 utilized 2N sodium hydroxide instead of 1N sodium hydroxide. $^1$H-NMR verified the formation of the desired adducts as the sodium salts.

Prep. Ex. 25

L-aspartic acid/VDM (number of spacer atoms=6 and 7; having two hydrogen bond donors): $^1$H-NMR (D$_2$O) δ 1.32 & 1.33 (2s, 6H), 2.41 (m, 2H), 4.17 (m, 1H), 5.56 (d, 1H), 6.03 (m, 2H)

Prep. Ex. 26

L-asparagine/VDM (number of spacer atoms=6; having four hydrogen bond donors): $^1$H-NMR (D$_2$O) δ 1.31 (2s, 6H), 2.51 (m, 2H), 4.25 (m, 1H), 5.56 (d, 1H), 6.03 (m, 2H)

Prep. Ex. 27

L-glutamic acid/VDM (number of spacer atoms=6 and 8; having two hydrogen bond donors): $^1$H-NMR (D$_2$O) δ 1.37 & 1.38 (2s, 6H), 1.75 (m, 1H), 1.89 (m, 1H), 2.04 (m, 2H), 3.98 (m, 1H), 5.62 (d, 1H), 6.05 (d, 1H), 6.17 (dd, 1H)

Prep. Ex. 28

L-glutamine/VDM (number of spacer atoms=6; having four hydrogen bond donors): $^1$H-NMR (D$_2$O) δ 1.31 & 1.33 (2s, 6H), 1.73 (m, 1H), 1.92 (m, 1H), 2.08 (m, 2H), 3.98 (m, 1H), 5.58 (d, 1H), 6.05 (m, 2H)

Prep. Ex. 29

L-aspartic acid/IEM (number of spacer atoms=8 and 9; having two hydrogen bond donors): $^1$H-NMR (D$_2$O) δ 1.73 (s, 3H), 2.26 (dd, 1H), 2.44 (dd, 1H), 3.26 (m, 2H), 4.03 (t & m, 3H), 5.52 (s, 1H), 5.95 (s, 1H)

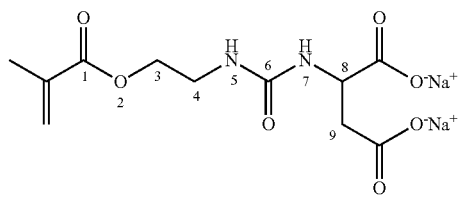

Prep. Ex. 30

L-asparagine/IEM (number of spacer atoms=8; having four hydrogen bond donors): $^1$H-NMR (D$_2$O) δ 1.73 (s, 3H), 2.40 (dd, 1H), 2.54 (dd, 1H), 3.26 (m, 2H), 4.03 (t, 2H), 4.15 (dd, 1H), 5.52 (s, 1H), 5.94 (s, 1H)

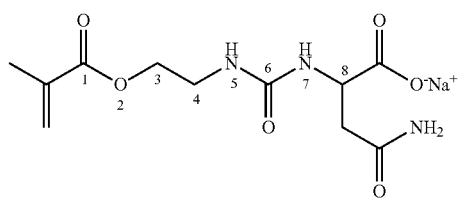

Prep. Ex. 31

L-glutamic acid/IEM (number of spacer atoms=8 and 10; having two hydrogen bond donors): $^1$H-NMR (D$_2$O) δ 1.63 (m 1H), 1.72 (s, 3H), 1.80 (m, 1H), 2.00 (m, 2H), 3.26 (m, 2H), 3.79 (m, 1H), 4.03 (m, 2H), 5.51 (s, 1H), 5.93 (s, 1H)

Prep. Ex. 32

L-glutamine/IEM (number of spacer atoms=8; having four hydrogen bond donors): $^1$H-NMR (D$_2$O) δ 1.72 (m, 1H), 1.73 (s, 3H), 1.87 (m, 1H), 2.10 (m, 2H), 3.27 (m, 2H), 3.86 (m, 1H), 4.04 (t, 2H), 5.52 (s, 1H), 5.94 (s, 1H)

Prep. Ex. 33 iminodiacetic acid/IEM (number of spacer atoms=8; having one hydrogen bond donor): $^1$H-NMR (D$_2$O) δ 1.74 (s, 3H), 3.29 (t, 2H), 3.64 (s, 4H), 4.03 (t, 2H), 5.53 (s, 1H), 5.96 (s, 1H)

Preparative Example 34

2-(Dimethylamino)ethanol (1.78 g, 0.02 mol, Alfa Aesar, Ward Hill, Mass.) was charged to a 25 mL glass vial. VDM (2.78 g, 0.02 mol) was added to the vial, followed by 1,8-diazabicyclo[5.4.0]undec-7-ene (DBU; 2 drops; available from Sigma-Aldrich, St. Louis, Mo.). The vial was sealed, and the contents of the vial were mixed by shaking.

A mild exotherm ensued, and the exotherm was mediated by holding the vial under cold running tap water for a few minutes. The vial was placed on a rocker for 1 hour, at which time NMR indicated complete conversion to the expected acrylamidoester product (having 7 spacer atoms, and having one hydrogen bond donor). $^1$H-NMR (CD$_3$OD) δ 1.47 (s, 6H), 2.26 (s, 6H), 2.60 (t, 2H), 4.20 (t, 2H) 5.63 (dd, 1H), 6.21 (m, 2H).

Preparative Examples 35-37

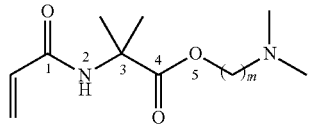

By procedures essentially analogous to that of Preparative Example 34, additional monomers (having spacer groups of chain length=5+m, wherein m varies, and having one hydrogen bond donor) were prepared from the following aminoalcohols:

Prep. Ex. 35

3-(dimethylamino)-1-propanol (m=3; number of spacer atoms=8): $^1$H-NMR (CD$_3$OD) δ 1.46 (s, 6H), 1.79 (m, 2H), 2.21 (s, 6H), 2.35 (m, 2H), 4.11 (t, 2H), 5.64 (dd, 1H), 6.21 (m, 2H)

Prep. Ex. 36

6-(dimethylamino)-1-hexanol (m=6; number of spacer atoms=11): $^1$H-NMR (CD$_3$OD) δ 1.33 (m, 4H), 1.46 (s and m, 8H), 1.61 (m, 2H), 2.22 (s, 6H), 2.29 (m, 2H), 4.07 (t, 2H), 5.63 (dd, 1H), 6.20 (m, 2H)

Prep. Ex. 37

2-[2-(dimethylamino)ethoxy]ethanol (TCI, Ltd., Tokyo, Japan) (m=4 plus one ether oxygen in repeat unit; number of spacer atoms=10): $^1$H-NMR (CD$_3$OD) δ 1.47 (s, 6H), 2.25 (s, 6H), 2.51 (t, 2H), 3.57 (t, 2H), 3.62 (m, 2H), 4.21 (m, 2H), 5.63 (dd, 1H), 6.20 (m, 2H)

Preparative Example 38

The monomer (a tertiary amine) from Preparative Example 34 (1.71 g, 7.5 mmol) was dissolved in diethyl ether (25 mL) in a 100 mL round bottomed flask. Dimethylsulfate (0.945 g, 0.72 mL, 7.5 mmol) was added by syringe to the magnetically stirred solution. A colorless precipitate formed immediately. The resulting mixture was allowed to stand overnight at room temperature. The precipitate was broken up with a spatula, filtered, washed with ether, and dried under vacuum at room temperature for about 1 hour to provide an essentially quantitative yield of the expected monomer (having 7 spacer atoms), a quaternary ammonium salt. $^1$H-NMR (D$_2$O) δ 1.38 (s, 6H), 3.05 (s, 9H), 3.62 (s and m, 5H), 4.47 (m, 2H), 5.67 (d, 1H), 6.10 (m, 2H). The monomer was dissolved in deionized water (10 mL) to prepare a monomer solution.

Preparative Examples 39-41

By procedures essentially analogous to that of Preparative Example 38, additional quaternary ammonium salt monomers were prepared from the following tertiary amine monomers. In these examples, the precipitates were not filtered, but rather the diethyl ether was removed by rotary evaporation, the residue was dried under vacuum at room temperature for 4 hours, and the dried residue was dissolved in deionized water (10 mL) to provide a monomer solution:

Prep. Ex. 39

Prep. Ex. 35 monomer (number of spacer atoms=8): $^1$H-NMR (D$_2$O) δ 1.37 (s, 6H), 2.07 (m, 2H), 3.00 (s, 9H), 3.25 (m, 2H), 3.61 (s, 3H), 4.13 (t, 2H), 5.67 (d, 1H), 6.12 (m, 2H)

Prep. Ex. 40

Prep. Ex. 36 monomer (number of spacer atoms=11): $^1$H-NMR (D$_2$O) δ 1.27 (m, 4H), 1.36 (s, 6H), 1.55 (m, 2H), 1.65 (m, 2H), 2.97 (s, 9H), 3.17 (m, 2H), 3.62 (s, 3H), 4.03 (t, 2H), 5.65 (d, 2H), 6.10 (m, 2H)

Prep. Ex. 41

Prep. Ex. 37 monomer (number of spacer atoms=10): $^1$H-NMR (D$_2$O) δ 1.37 (s, 6H), 3.06 (s, 9H), 3.45 (m, 2H), 3.62 (s, 3H), 3.67 (m, 2H), 3.85 (m, 2H), 4.20 (m, 2H), 5.66 (d, 1H), 6.10 (m, 2H)

Preparative Examples 42-43

Monomers were prepared from taurine (2-aminoethylsulfonic acid) by essentially the procedures described in Preparative Examples 1 and 12, using either VDM or IEM, respectively. $^1$H-NMR verified the formation of the desired adducts as the sodium salts.

Prep. Ex. 42 taurine/VDM (number of spacer atoms=7, and having two hydrogen bond donors): $^1$H-NMR (D$_2$O) δ 1.35 (s, 6H), 2.94 (t, 2H), 3.45 (t, 2H) 5.64 (m, 1H), 6.10 (m, 2H)

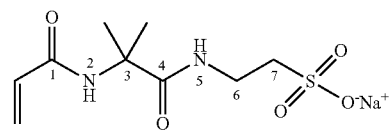

Prep. Ex. 43 taurine/IEM (number of spacer atoms=9, and having two hydrogen bond donors): $^1$H-NMR (D$_2$O) δ 1.75 (s, 3H), 2.88 (t, 2H), 3.28 (t, 2H), 3.32 (t, 2H), 4.06 (t, 2H), 5.56 (2, 1H), 5.97 (s, 1H)

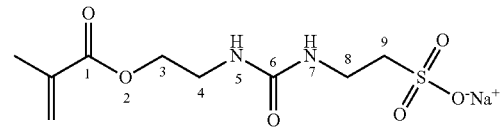

Preparative Example 44

A monomer (having 8 spacer atoms and one hydrogen bond donor) was prepared from IEM and N-benzylglycine (Sigma-Aldrich, St. Louis, Mo.) by essentially the procedure described in Preparative Example 12. $^1$H-NMR (D$_2$O) δ 1.66 (s, 3H), 3.32 (t, 2H), 3.66 (s, 2H), 3.98 (t, 2H), 4.32 (s, 2H), 5.48 (s, 1H), 5.86 (s, 1H), 7.04 (d, 2H), 7.13 (m, 1H), 7.17 (m 2H).

Preparative Example 45

2-(Dimethylamino)ethanol (1.78 g, 0.02 mol) was charged to a 100 mL round bottom flask. Diethylether (20 mL) was added to the flask, and the resulting mixture was stirred magnetically until the alcohol dissolved. IEM (3.10 g, 0.02 mol) was added to the flask, and the resulting mixture was stirred at room temperature for 3 hours to obtain the expected urethane monomer product (having 9 spacer atoms and one hydrogen bond donor). $^1$H-NMR (CDCl$_3$) δ 1.86 (s, 3H), 2.19 (s, 6H), 2.46 (t, 2H), 3.41 (m, 2H), 4.08 (t, 2H) 4.13 (t, 2H), 5.51 (s, 1H), 6.03 (s, 1H).

Preparative Example 46(a)

2-[2-(Dimethylamino)ethoxy]ethanol (2.66 grams, 0.02 mol) was converted to the corresponding methacrylate urethane monomer (having 12 spacer atoms and one hydrogen bond donor) by essentially the procedure of Preparative Example 45. $^1$H-NMR (CDCl$_3$) δ 1.82 (s, 3H), 2.14 (s, 6H), 2.39 (t, 2H), 3.37 (m, 2H), 3.45 (t, 2H), 3.53 (m, 2H), 4.10 (m, 4H), 5.38 (br. s, ca. 1H), 5.48 (s, 1H), 6.00 (s, 1H).

Preparative Example 46(b)

Preparative Example 46(a) was repeated. The reaction mixture was poured into a separatory funnel, followed by a 1N hydrochloric acid solution (20 mL). The resulting mixture was intimately mixed by shaking and then allowed to phase separate, and the resulting lower aqueous phase was separated. NMR analysis indicated that the methacrylate urethane monomer (having 12 spacer atoms and one hydrogen bond donor) had been extracted into the aqueous phase as the hydrochloride salt. $^1$H-NMR (D$_2$O) δ 1.74 (s, 3H), 2.73 (s, 6H), 3.18 (t, 2H), 3.28 (t, 2H), 3.58 (m, 2H), 3.67 (m, 2H), 4.06 (m, 4H), 5.55 (s, 1H), 5.95 (s, 1H).

Preparative Example 47

The reaction mixture from Preparative Example 46(a) was cooled in an ice-water bath for 15 minutes. Dimethylsulfate (2.52 grams, 0.02 mole) was added to the mixture by syringe. An exothermic reaction ensued, and an oily precipitate appeared. The resulting mixture was stirred at room temperature for 1 hour, the resulting ether supernate was poured off, and the resulting residue was stripped on a rotary evaporator for an additional 30 minutes to yield the expected quaternary ammonium salt monomer (having 12 spacer atoms and one hydrogen bond donor) as a viscous oil. $^1$H-NMR (D$_2$O) δ 1.74 (s, 3H), 3.00 (s, 9H), 3.28 (t, 2H), 3.41 (m, 2H), 3.56 (s, 3H), 3.58 (m, 2H), 3.81 (m, 2H), 4.06 (m, 4H), 5.56 (s, 1H), 5.95 (s, 1H).

Preparative Example 48

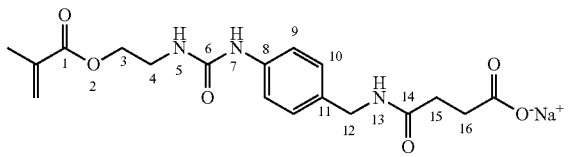

A 250 mL round bottom flask was charged with ethanol (50 mL) and succinic anhydride (2.00 grams, 0.02 mol). The resulting mixture was stirred magnetically until the anhydride dissolved. 4-Aminobenzylamine (2.44 grams, 0.02 mol) was added to the flask. The resulting mixture was stirred for 5 days. An off-white solid precipitated and was filtered, washed with diethylether, and dried under vacuum. $^1$H-NMR (D$_2$O) δ 2.32 (m, 4H), 4.13 (s, 2H), 6.93 (d, 2H) 7.09 (d, 2H).

A portion of the dried product (0.5 grams, 2.25 mmol) was dissolved in 2.25 grams of 1N NaOH, and the resulting solution was stirred magnetically and cooled in an ice-water bath for 15 minutes. IEM (0.35 grams, 2.25 mmol) was added to the solution. The resulting mixture was stirred and allowed to warm to room temperature over 4.5 hours. A resulting small amount of colorless precipitate was filtered. NMR analysis indicated clean formation of the desired carboxylic acid methacrylate monomer (having 16 spacer atoms, as shown in the above structure, and three hydrogen bond donors). $^1$H-NMR (D$_2$O) δ 1.71 (s, 3H), 2.30 (m, 4H), 3.31 (t, 2H), 4.05 (t, 2H), 4.13 (s, 2H), 5.50 (s, 1H), 5.93 (s, 1H), 7.04 (m, 4H).

Preparative Comparative Example 1

Sodium acrylate (Sigma-Aldrich, St. Louis, Mo.; 4.70 g, 0.05 mol) was dissolved in deionized water (50 mL) to prepare a monomer (having zero spacer atoms) solution essentially equivalent in concentration to those of Preparative Examples 1-8.

Preparative Comparative Example 2

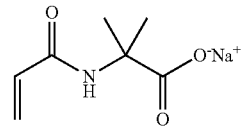

N-acryloyl-2-methylalanine, prepared essentially according to Example 7 of U.S. Pat. No. 4,157,418 (Heilmann) (7.85 g, 0.05 mol) was dissolved in sodium hydroxide solution (1 N, 50 mL) to prepare a monomer (having 3 spacer atoms and one hydrogen bond donor) solution essentially equivalent in concentration to those of Preparative Examples 1-8.

Preparative Comparative Example 3

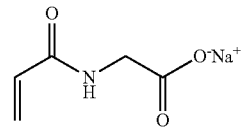

N-acryloylglycine, prepared essentially according to Example 1 of U.S. Pat. No. 4,157,418 (Heilmann) (6.45 g., 0.05 mol) was dissolved in sodium hydroxide solution (1 N, 50 mL) to prepare a monomer (having 3 spacer atoms and one hydrogen bond donor) solution essentially equivalent in concentration to those of Preparative Examples 1-8.

Preparative Comparative Example 4

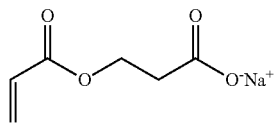

2-Carboxyethylacrylate (Sigma-Aldrich, St. Louis, Mo.; 7.2 g, 0.05 mol) was dissolved in sodium hydroxide solution (1 N, 50 mL) to prepare a monomer (having 4 spacer atoms) solution essentially equivalent in concentration to those of Preparative Examples 1-8.

Preparative Comparative Example 5

Methacrylic acid (4.30 g, 0.05 mol) was dissolved in sodium hydroxide solution (1N, 50 mL) to prepare a monomer (having zero spacer atoms) solution essentially equivalent in concentration to those of Preparative Examples 12-22.

Preparative Comparative Example 6

[2-(Methacryloyloxy)ethyl]trimethylammonium chloride (Sigma-Aldrich, St. Louis, Mo.; 13.85 g of a 75 percent (%) by weight solution in water) was diluted with deionized water (36 mL) to prepare a monomer (having 4 spacer atoms) solution of essentially equivalent molar concentration to that of Preparative Example 23.

Preparative Comparative Example 7

The solution from Preparative Comparative Example 6 (3.75 grams) was diluted with deionized water (1.25 grams).

Preparative Comparative Example 8

[3-(Methacryloylamino)propyl]trimethylammonium chloride (Sigma-Aldrich, St. Louis, Mo.; 22.07 g of a 50 percent (%) by weight solution in water) was diluted with deionized water (27.9 g) to prepare a monomer (having 5 spacer atoms and one hydrogen bond donor) solution of essentially equivalent molar concentration to that of Preparative Example 24.

Preparative Comparative Example 9

The solution from Preparative Comparative Example 8 (3.75 grams) was diluted with deionized water (1.25 grams).

Preparative Comparative Example 10

3-(Acrylamidopropyl)trimethylammonium chloride (Sigma-Aldrich, St. Louis, Mo.; 2.07 g of a 75 percent (%) by weight solution in water) was diluted with deionized water (9.5 g) to prepare a monomer (having 5 spacer atoms and one hydrogen bond donor) solution of essentially equivalent molar concentration to those of Examples 38-41.

Preparative Comparative Example 11

2-Acrylamido-2-methyl-1-propanesulfonic acid, sodium salt (Sigma-Aldrich, St. Louis, Mo.; 41.34 g of a 50 percent (%) by weight solution in water) was diluted with deionized water (79.3 g) to prepare a monomer (having 4 spacer atoms and one hydrogen bond donor) solution of essentially equivalent concentration to those of Preparative Examples 42 and 43.

Preparative Comparative Example 12

N-acryloylphenylalanine, prepared essentially according to Example 10 of U.S. Pat. No. 4,157,418 (Heilmann) (10.95 g, 0.05 mol) was dissolved in sodium hydroxide solution (1 N, 50 mL) to prepare a monomer (having 3 spacer atoms and one hydrogen bond donor) solution essentially equivalent in concentration to those of Preparative Examples 1-8.

Examples 1-6 and Comparative Examples C-1-C-4

Coating solutions were prepared by mixing monomer solutions from each of Preparative Examples 1-4, 7, and 8 and Preparative Comparative Examples 1-4 (3.75 g) with deionized water (1.25 g) and S-BP (250 µL of a 0.1 g/mL solution in deionized water). For each coating solution, a nylon membrane substrate (9 cm×12 cm; nylon 66 membrane, single reinforced layer nylon three-zone membrane, nominal pore size 1.8 µm, #080ZN, obtained from 3M Purification, Inc., Meridan, Conn.) was placed on a sheet of polyester film, and approximately 4.5 mL of coating solution was pipetted onto the top surface of the substrate. The coating solution was allowed to soak into the substrate for about 1 minute, and then a second sheet of polyester film was placed on top of the substrate. A 2.28 kg cylindrical weight was rolled over the top of the resulting three-layer sandwich to squeeze out excess coating solution. Ultraviolet (UV)-initiated grafting was conducted by irradiating the sandwich using a UV stand (Classic Manufacturing, Inc., Oakdale, Minn.) equipped with 18 bulbs (Sylvania RG2 40 W F40/350BL/ECO, 10 above and 8 below the substrate, 1.17 meters (46 inches) long, spaced 5.1 cm (2 inches) on center), with an irradiation time of 15 minutes. The polyester sheets were removed, and the resulting functionalized substrate was placed in a 250 mL polyethylene bottle. The bottle was filled with 0.9 percent (%) saline, sealed, and shaken for 30 minutes to wash off any residual monomer or ungrafted polymer. The saline was poured off, and the functionalized substrate was washed for another 30 minutes with fresh saline solution and then washed for 30 minutes with deionized water and allowed to dry.

The functionalized substrate was tested for graft density and static lysozyme binding capacity, from which ligand efficiency was calculated. Results are reported in Table 1(a) below for each coating solution. In order to minimize the effects of experimental variability, the substrate functionalization procedure was often repeated and the results of the number of repetitions (N) averaged to provide the reported values.

TABLE 1(a)

| Example No. | Monomer | Graft Density (mmol/g) | Lysozyme Static Capacity (mg/mL) | Ligand Efficiency (capacity/ mmol/g) | N | Number of Spacer Atoms |
|---|---|---|---|---|---|---|
| 1 | Prep. Ex. 1 | 0.64 | 151 | 237 | 3 | 6 |
| 2 | Prep. Ex. 2 | 0.62 | 176 | 281 | 3 | 7 |
| 3 | Prep. Ex. 3 | 0.49 | 139 | 283 | 3 | 8 |
| 4 | Prep. Ex. 4 | 0.61 | 177 | 291 | 3 | 10 |
| 5 | Prep. Ex. 7 | 0.49 | 141 | 288 | 2 | 9 |
| 6 | Prep. Ex. 8 | 0.44 | 145 | 329 | 2 | 12 |

TABLE 1(a)-continued

| Example No. | Monomer | Graft Density (mmol/g) | Lysozyme Static Capacity (mg/mL) | Ligand Efficiency (capacity/ mmol/g) | N | Number of Spacer Atoms |
|---|---|---|---|---|---|---|
| C-1 | Prep. Comp. Ex. 1 | 0.44 | 40 | 90 | 3 | 0 |
| C-2 | Prep. Comp. Ex. 2 | 0.75 | 118 | 159 | 3 | 3 |
| C-3 | Prep. Comp. Ex. 3 | 0.81 | 152 | 190 | 3 | 3 |
| C-4 | Prep. Comp. Ex. 4 | 0.57 | 102 | 179 | 2 | 4 |

Several of the functionalized substrates were also tested for static IgG capacity (IgG Method 1) and corresponding ligand efficiencies calculated. Results are shown in Table 1(b).

TABLE 1(b)

| Example No. | IgG Static Capacity (mg/mL) | Ligand Efficiency (capacity/mmol/g) |
|---|---|---|
| 1 | 134 | 210 |
| 2 | 157 | 247 |
| 3 | 169 | 357 |
| 4 | 169 | 284 |
| C-1 | 123 | 148 |
| C-2 | 126 | 172 |
| C-3 | 63 | 165 |

Examples 7-14 and Comparative Example C-5

Coating solutions were prepared by mixing monomer solutions from each of Preparative Examples 12-18 and 22 and Preparative Comparative Example 5 (3.75 g) with deionized water (1.25 g) and S-BP (250 μL of a 0.1 g/mL solution in deionized water). Nylon membrane substrates were coated, grafted, washed, and evaluated essentially as described in Example 1. Results are shown in Table 2 below.

TABLE 2

| Example No. | Monomer | Graft Density (mmol/g) | Lysozyme Static Capacity (mg/mL) | Ligand Efficiency (capacity/ mmol/g) | N | Number of Spacer Atoms |
|---|---|---|---|---|---|---|
| 7 | Prep. Ex. 12 | 0.51 | 119 | 232 | 3 | 8 |
| 8 | Prep. Ex. 13 | 0.50 | 122 | 248 | 2 | 9 |
| 9 | Prep. Ex. 14 | 0.53 | 133 | 250 | 3 | 10 |
| 10 | Prep. Ex. 15 | 0.56 | 126 | 223 | 3 | 12 |
| 11 | Prep. Ex. 16 | 0.55 | 145 | 264 | 2 | 11 |
| 12 | Prep. Ex. 17 | 0.52 | 157 | 302 | 2 | 14 |
| 13 | Prep. Ex. 18 | 0.56 | 120 | 216 | 2 | 8 |
| 14 | Prep. Ex. 22 | 0.59 | 112 | 191 | 2 | 9 |
| C-5 | Prep. Comp. Ex. 5 | 0.36 | 36 | 102 | 3 | 0 |

Example 15

Preparation and Grafting of the Poly(ethylene glycol)(200) monomethylacrylate Ester of Glutaric Acid Glutaric anhydride (3.50 g, 0.03 mol) was charged to a 100 mL round bottom flask, and dichloromethane (50 mL) was added to the flask. The resulting mixture was stirred magnetically until the anhydride dissolved, and then PEG200MA (6.70 g, 0.025 mol) was added to the flask. The resulting mixture was stirred for 15 minutes and then cooled in an ice-water bath to 0° C. Triethylamine (3.1 g, 4.3 mL, 0.03 mol) was added by syringe to the stirring mixture, then 4-dimethylaminopyridine (0.06 g, 0.03 mol) was also added. The resulting mixture was stirred for 2 hours with ice-bath cooling and then allowed to warm to room temperature over 30 minutes. The resulting mixture was stirred for an additional 12 hours at room temperature.

Excess solvent was removed from the mixture by rotary evaporation. The resulting residue was dissolved in diethyl ether, and product was extracted from the resulting solution into a saturated sodium bicarbonate (3×50 mL) phase. The final pH of the phase (basic solution) was adjusted to 2 by adding 1N HCl. Then, the product was extracted from the resulting acidic aqueous phase into a diethyl ether (3×100 mL) phase, which was then washed with brine and dried over $Na_2SO_4$. Excess solvent was removed from the diethyl ether phase by rotary evaporation to yield the product as a colorless liquid. $^1$H-NMR (DMSO-$d_6$) δ 1.71, 1.88, 2.24, 2.33, 3.49, 3.63, 4.12, 4.20, 4.28, 5.68, 6.02 indicated complete conversion to the desired carboxylic acid monomer having approximately 18 spacer atoms and no hydrogen bond donors. When the monomer was grafted to a nylon membrane substrate essentially as described in Example 1, the resulting functionalized substrate displayed lysozyme binding capacity similar to that of Example 14.

Examples 16-19 and Comparative Examples C-6-C-9

Coating solutions were prepared as follows. For Examples 16 and 18 and Comparative Examples C-6 and C-8, the monomer solutions from Preparative Examples 23 and 24 and Comparative Examples 6 and 8 (5 grams) were each mixed with S-BP (250 μL of a 0.1 g/mL solution in deionized water). For Examples 17 and 19, each monomer solution (3.75 grams) was diluted with deionized water (1.25 g) prior to mixing with the S-BP solution. For Comparative Examples C-7 and C-9, the S-BP solution was added directly to the respective monomer solutions before coating. Nylon membrane substrates were coated, grafted, washed, and evaluated essentially as described in Example 1, except that BSA static binding capacity was measured. Results are shown in Table 3.

TABLE 3

| Example No. | Monomer | Graft Density (mmol/g) | BSA Static Capacity (mg/mL) | Ligand Efficiency (capacity/ mmol/g) | N | Number of Spacer Atoms |
|---|---|---|---|---|---|---|
| 16 | Prep. Ex. 23 | 0.62 | 133 | 215 | 1 | 9 |
| 17 | Prep. Ex. 23 | 0.44 | 96 | 219 | 1 | 9 |
| 18 | Prep. Ex. 24 | 0.60 | 154 | 258 | 1 | 7 |
| 19 | Prep. Ex. 24 | 0.42 | 132 | 316 | 1 | 7 |
| C-6 | Prep. Comp. Ex. 6 | 0.89 | 146 | 164 | 1 | 4 |
| C-7 | Prep. Comp. Ex. 7 | 0.57 | 94 | 166 | 1 | 4 |
| C-8 | Prep. Comp. Ex. 8 | 1.03 | 137 | 133 | 1 | 5 |
| C-9 | Prep. Comp. Ex. 9 | 0.54 | 78 | 143 | 1 | 5 |

Examples 20-23 and Comparative Example C-10

Coating solutions were prepared by mixing monomer solutions from each of Preparative Examples 1-4 and Preparative Comparative Example 2 (20 g) with MBA (1.2 mL of a 0.1 g/mL solution in methanol), PEG400MA (1.6 g), and S-BP (1.0 mL of a 0.1 g/mL solution in deionized water). Nylon membrane substrates were coated, grafted, and washed essentially as described in Example 1, except that the time of UV irradiation was only 10 minutes. The resulting functionalized substrates were tested for static lysozyme and IgG (IgG Method 2) binding capacities, and the results are shown in Table 4.

TABLE 4

| Example No. | Monomer | Lysozyme Static Capacity (mg/mL) | IgG Static Capacity (mg/mL) |
|---|---|---|---|
| 20 | Prep. Ex. 1 | 215 | 213 |
| 21 | Prep. Ex. 2 | 276 | 242 |
| 22 | Prep. Ex. 3 | 309 | 243 |
| 23 | Prep. Ex. 4 | 354 | 119 |
| C-10 | Prep. Comp. Ex. 2 | 198 | 130 |

Examples 24-32

Coating solutions were prepared by mixing monomer solutions from each of Preparative Examples 25-33 (3.75 g) with deionized water (1.25 g) and S-BP (250 µL of a 0.1 g/mL solution in deionized water). Nylon membrane substrates were coated, grafted, washed, and evaluated essentially as described in Example 1. Results are shown in Table 5(a).

TABLE 5(a)

| Example No. | Monomer | Graft Density (mmol/g) | Lysozyme Static Capacity (mg/mL) | Ligand Efficiency (capacity/mmol/g) | N | Number of Spacer Atoms |
|---|---|---|---|---|---|---|
| 24 | Prep. Ex. 25 | 0.48 | 73 | 151 | 1 | 6, 7 |
| 25 | Prep. Ex. 26 | 0.57 | 89 | 156 | 1 | 6 |
| 26 | Prep. Ex. 27 | 0.58 | 124 | 213 | 1 | 6, 8 |
| 27 | Prep. Ex. 28 | 0.50 | 95 | 189 | 1 | 6 |
| 28 | Prep. Ex. 29 | 0.41 | 58 | 139 | 1 | 8, 9 |
| 29 | Prep. Ex. 30 | 0.42 | 129 | 306 | 1 | 8 |
| 30 | Prep. Ex. 31 | 0.38 | 75 | 199 | 1 | 8, 10 |
| 31 | Prep. Ex. 32 | 0.48 | 139 | 292 | 1 | 8 |
| 32 | Prep. Ex. 33 | 0.43 | 87 | 203 | 1 | 8 |

The resulting functionalized substrates were also tested for static IgG capacities (IgG Method 1) and corresponding ligand efficiencies calculated. Results, showing relatively high capacities and efficiencies for IgG capture, are shown in Table 5(b).

TABLE 5(b)

| Example No. | IgG Static Capacity (mg/mL) | Ligand Efficiency (capacity/mmol/g) |
|---|---|---|
| 24 | 183 | 381 |
| 25 | 173 | 303 |
| 26 | 169 | 290 |
| 27 | 188 | 373 |
| 28 | 187 | 453 |
| 29 | 179 | 426 |
| 30 | 204 | 541 |
| 31 | 196 | 412 |
| 32 | 192 | 449 |

Examples 33-36 and Comparative Example C-11

Coating solutions were prepared by mixing monomer solutions from each of Preparative Examples 38-41 and Preparative Comparative Example 10 (5.0 g) with S-BP (250 µL of a 0.1 g/mL solution in deionized water). Nylon membrane substrates were coated, grafted, washed, and evaluated essentially as described in Example 16. Results are shown in Table 6.

TABLE 6

| Example No. | Monomer | BSA Static Capacity (mg/mL) | Number of Spacer Atoms |
|---|---|---|---|
| 33 | Prep. Ex. 38 | 145 | 7 |
| 34 | Prep. Ex. 39 | 166 | 8 |
| 35 | Prep. Ex. 40 | 161 | 11 |
| 36 | Prep. Ex. 41 | 168 | 10 |
| C-11 | Prep. Comp. Ex. 10 | 121 | 5 |

Examples 37-38 and Comparative Example C-12

Coating solutions were prepared as follows. For Examples 37 and 38 and Comparative Example 12, the monomer solutions from Preparative Examples 42 and 43 and Preparative Comparative Example 11 (5 grams) were each mixed with S-BP (250 µL of a 0.1 g/mL solution in deionized water). Nylon membrane substrates were coated, grafted, washed, and evaluated essentially as described in Example 1. Results are shown in Table 7.

TABLE 7

| Example No. | Monomer | Graft Density (mmol/g) | Lysozyme Static Capacity (mg/mL) | Ligand Efficiency (capacity/mmol/g) | N | Number of Spacer Atoms |
|---|---|---|---|---|---|---|
| 37 | Prep. Ex. 42 | 0.41 | 147 | 356 | 1 | 7 |
| 38 | Prep. Ex. 43 | 0.50 | 153 | 303 | 1 | 9 |
| C-12 | Prep. Comp. Ex. 11 | 1.19 | 143 | 120 | 1 | 4 |

Example 39

The monomer solution of Preparative Example 48 was formulated, coated, grafted, washed, and evaluated essentially as described in Example 1. As the average of three trials, the resulting substrates functionalized with this monomer, having a spacer length of 16 atoms, exhibited a graft density of 1.01 mmol/g, lysozyme static capacity of 195 mg/mL, and a ligand efficiency of 193.

Example 40

The monomer solution of Preparative Example 46(b) (3.75 g) was mixed with deionized water (1.25 g) and S-BP (250 μL of a 0.1 g/mL solution in deionized water). Nylon membrane substrates were coated, grafted, washed, and dried essentially as described in Example 1. Static BSA capacity was measured as described above, except that the TRIS buffer was replaced by 10 millimolar MOPS (3-(N-morpholino)propanesulfonic acid; Sigma-Aldrich, St. Louis, Mo.), pH 7.5. Under these conditions, graft density was 0.75 mmol/g, BSA capacity was 74.9 mg/mL, and ligand efficiency was 159.

Example 41 and Comparative Example C-13

Coating solutions were prepared by mixing monomer solutions from each of Preparative Example 9 and Preparative Comparative Example 12 (3.75 g) with deionized water (1.25 g) and S-BP (250 μL of a 0.1 g/mL solution in deionized water). Nylon membrane substrates were coated, grafted, washed, and evaluated essentially as described in Example 1. Results are shown in Table 8.

TABLE 8

| Example No. | Monomer | Graft Density (mmol/g) | Lysozyme Static Capacity (mg/mL) | Ligand Efficiency (capacity/mmol/g) | N | Number of Spacer Atoms |
| --- | --- | --- | --- | --- | --- | --- |
| 41 | Prep. Ex. 9 | 0.56 | 113 | 204 | 2 | 6 |
| C-13 | Prep. Comp. Ex. 12 | 0.41 | 58 | 143 | 3 | 3 |

Example 42

Preparation and Grafting of Phosphonate Monomer

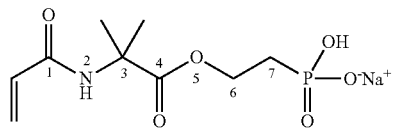

Ex. 42(a)—2-Dimethoxyphosphorylethyl-2-methyl-2-(prop-2-enoylamino)propanoate A solution of VDM (1.63 g, 11.7 mmol) in 10 mL of anhydrous methylene chloride was treated with hydroxyethyl dimethylphosphonate (90 percent (%) purity, 2.00 g, 11.7 mmol) and one drop of 1,8-diazabicyclo[5.4.0]undec-7-ene (DBU; available from Sigma-Aldrich, St. Louis, Mo.). After stirring overnight, the resulting mixture was diluted with methylene chloride and washed successively with saturated 5% $NaH_2PO_4$, $H_2O$, and brine. The resulting organic portion was dried over $Na_2SO_4$ and filtered. A small amount (approximately 3 mg) of 2,6-di-tert-butyl-4-methylphenol (BHT; Sigma-Aldrich, St. Louis, Mo.) was added to the filtered portion, and the resulting solution was concentrated under reduced pressure at ambient temperature (about 23° C.) to give 3.06 g of colorless liquid. $^1$H NMR ($CDCl_3$, 500 MHz) □ 6.35 (br s, 1H), 6.27 (dd, J=1.4, 17.0 Hz, 1H), 6.12 (dd, J=10.2, 17.0 Hz, 1H), 5.64 (dd, J=1.4, 10.2 Hz, 1H), 4.39 (dt, J=13.3, 7.3 Hz, 2H), 3.77 (d, J=10.9 Hz, 6H), 2.19 (dt, J=18.8, 7.3 Hz, 2H), 1.60 (s, 6H).

Ex. 42(b)—2-[2-Methyl-2-(prop-2-enoylamino)propanoyl]oxyethylphosphonic Acid, Sodium Salt The above-prepared colorless liquid (3.06 g, 10.4 mmol) was dissolved in 10 mL of anhydrous methylene chloride and treated with trimethylsilyl bromide (3.24 g, 21.2 mmol). The resulting solution was stirred for 3 hours and then concentrated under reduced pressure at ambient temperature (about 23° C.). The resulting oil was then concentrated from methanol twice to give 2.77 g of colorless syrup. $^1$H NMR ($D_2O$, 500 MHz) □ 6.15 (dd, J=10.1, 17.1 Hz, 1H), 6.06 (dd, J=1.4, 17.1 Hz, 1H), 5.55 (dd, J=1.4, 10.1 Hz, 1H), 4.25 (dt, J=15.1, 7.1 Hz, 2H), 2.09 (dt, J=18.2, 7.1 Hz, 2H), 1.38 (s, 6H). The syrup was dissolved in 1N sodium hydroxide (10.45 mL) to prepare a monomer solution comprising the monomer shown above, having seven spacer atoms and one hydrogen bond donor. The monomer solution was formulated, coated, grafted, washed, and evaluated essentially as described in Example 1. The resulting substrate functionalized with this monomer exhibited a graft density of 0.46 mmol/g, a lysozyme static capacity of 179 mg/mL, and a ligand efficiency of 391.

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows.

We claim:
1. An article for biomaterial capture comprising
   (a) a porous polymeric membrane; and
   (b) grafted to said porous polymeric membrane, a polymer comprising interpolymerized units of at least one monomer of the formula:

$CH_2=CR^1—C(=O)—X—R^2—[Z—R^2]_n-L$ wherein
   $R^1$ is selected from hydrogen, alkyl, cycloalkyl, aryl, and combinations thereof;
   each $R^2$ is independently selected from hydrocarbylene, heterohydrocarbylene, and combinations thereof;
   X is —O— or —$NR^3$—, where $R^3$ is selected from hydrogen, hydrocarbyl, heterohydrocarbyl, and combinations thereof;
   Z is heterohydrocarbylene comprising at least one hydrogen bond donor, at least one hydrogen bond acceptor, or a combination thereof;
   n is 1; and
   L is a heteroatom-containing group comprising at least one monovalent ligand functional group selected from acidic groups, basic groups other than guanidino, and salts thereof.

2. The article of claim 1 wherein said article comprises at least one filter element.

3. A process for capture or removal of a target biomaterial comprising
   (a) providing at least one article of claim 1; and
   (b) allowing a moving biological solution containing a target biomaterial to impinge upon the upstream surface of said filter element for a time sufficient to effect binding of said target biomaterial.

4. The process of claim 3, wherein said target biological species is a protein.

\* \* \* \* \*